(12) United States Patent
Joseph et al.

(10) Patent No.: US 9,951,381 B2
(45) Date of Patent: Apr. 24, 2018

(54) APPARATUS FOR HIGH THROUGHPUT CHEMICAL REACTIONS

(71) Applicant: Takara Bio USA, Inc., Mountain View, CA (US)

(72) Inventors: Victor Joseph, Fremont, CA (US);
Amjad Huda, Fremont, CA (US);
Alnoor Shivji, Fremont, CA (US)

(73) Assignee: TAKARA BIO USA, INC., Mountain View, CA (US)

( * ) Notice: Subject to any disclaimer, the term of this patent is extended or adjusted under 35 U.S.C. 154(b) by 47 days.

(21) Appl. No.: 14/853,480

(22) Filed: Sep. 14, 2015

(65) Prior Publication Data

US 2016/0186235 A1    Jun. 30, 2016

Related U.S. Application Data

(60) Continuation of application No. 13/594,562, filed on Aug. 24, 2012, now Pat. No. 9,132,427, which is a division of application No. 12/009,953, filed on Jan. 22, 2008, now Pat. No. 8,252,581.

(60) Provisional application No. 61/016,377, filed on Dec. 21, 2007, provisional application No. 60/886,067, filed on Jan. 22, 2007.

(51) Int. Cl.
| | |
|---|---|
| *C12M 1/34* | (2006.01) |
| *G01N 21/00* | (2006.01) |
| *C12Q 1/68* | (2018.01) |
| *B01L 7/00* | (2006.01) |
| *G01N 21/25* | (2006.01) |
| *G01N 21/03* | (2006.01) |

(52) U.S. Cl.
CPC .............. *C12Q 1/686* (2013.01); *B01L 7/525* (2013.01); *B01L 7/5255* (2013.01); *G01N 21/253* (2013.01); *B01L 7/54* (2013.01); *B01L 2200/10* (2013.01); *B01L 2200/147* (2013.01); *B01L 2300/0654* (2013.01); *B01L 2300/0819* (2013.01); *B01L 2300/0829* (2013.01); *B01L 2300/0893* (2013.01); *B01L 2300/1805* (2013.01); *B01L 2300/1827* (2013.01); *B01L 2300/1844* (2013.01); *B01L 2300/1894* (2013.01); *G01N 21/0332* (2013.01)

(58) Field of Classification Search
CPC .......... C12M 1/34; G01N 21/00; B01L 7/525; B01L 2300/0829; B01L 2300/1805
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,210,015 A | 5/1993 | Gelfand et al. |
| 5,252,294 A | 10/1993 | Kroy et al. |
| 5,281,516 A | 1/1994 | Stapleton et al. |
| 5,338,671 A | 8/1994 | Scalice et al. |
| 5,342,581 A | 8/1994 | Sanadi |
| 5,475,610 A | 12/1995 | Atwood et al. |
| 5,494,810 A | 2/1996 | Barany et al. |
| 5,496,517 A | 3/1996 | Pfost et al. |
| 5,498,392 A | 3/1996 | Wilding et al. |
| 5,525,300 A | 6/1996 | Danssaert et al. |
| 5,552,321 A | 9/1996 | Focht |
| 5,552,580 A | 9/1996 | Pfost et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,602,756 A | 2/1997 | Atwood et al. |
| 5,639,423 A | 6/1997 | Northrup et al. |
| 5,656,493 A | 8/1997 | Mullis et al. |
| 5,674,743 A | 10/1997 | Ulmer |
| 5,716,842 A | 2/1998 | Baier et al. |
| 5,720,923 A | 2/1998 | Haff et al. |
| 5,721,136 A | 2/1998 | Finney et al. |
| 5,773,258 A | 6/1998 | Birch et al. |
| 5,779,977 A | 7/1998 | Haff et al. |
| 5,779,981 A | 7/1998 | Danssaert et al. |
| 5,827,480 A | 10/1998 | Haff et al. |
| 5,866,345 A | 2/1999 | Wilding et al. |
| 5,939,312 A | 8/1999 | Baier et al. |
| 5,955,029 A | 9/1999 | Wilding et al. |
| 5,985,555 A | 11/1999 | Bertling |
| 6,015,674 A | 1/2000 | Woudenberg et al. |
| 6,033,880 A | 3/2000 | Haff et al. |
| 6,054,263 A | 4/2000 | Danssaert et al. |
| 6,126,804 A | 10/2000 | Andresen |
| 6,132,580 A | 10/2000 | Mathies et al. |
| 6,153,426 A | 11/2000 | Heimberg et al. |
| 6,174,675 B1 | 1/2001 | Chow et al. |

(Continued)

FOREIGN PATENT DOCUMENTS

| | | |
|---|---|---|
| EP | 0438883 B1 | 5/1996 |
| EP | 0637999 B1 | 12/1998 |
| EP | 0739423 B1 | 1/2002 |
| EP | 1022059 B1 | 8/2002 |
| EP | 1013342 B1 | 4/2004 |
| EP | 0881950 B1 | 7/2004 |
| EP | 0871545 B1 | 1/2005 |
| EP | 1510823 A2 | 3/2005 |

(Continued)

OTHER PUBLICATIONS

Lin et al., "Fabrication of polydimethylsiloxane (PDMS) pulsating heat pipe" Applied Thermal Engineering Feb. 2009, 29(2-3): 573-580.

(Continued)

*Primary Examiner* — Randy Boyer
(74) *Attorney, Agent, or Firm* — Bozicevic, Field & Francis LLP; Bret E. Field

(57) ABSTRACT

Apparatus, systems, chips, and methods of performing a large number of simultaneous chemical reactions are provided herein. The chips of the invention comprise addressable units that can be addressed according to the temperature of the reaction to be run. The subject apparatus, systems, and chips are particularly suited for performing polymerase chain reactions on thousands of nucleic acid sequences, up to and including sequences of an entire genome of an organism of interest.

15 Claims, 19 Drawing Sheets

(56) References Cited

U.S. PATENT DOCUMENTS

| | | |
|---|---|---|
| 6,184,029 B1 | 2/2001 | Wilding et al. |
| 6,197,572 B1 | 3/2001 | Schneebeli |
| 6,284,525 B1 | 9/2001 | Mathies et al. |
| 6,303,343 B1 | 10/2001 | Kopf-sill |
| 6,306,590 B1 | 10/2001 | Mehta et al. |
| 6,309,886 B1 | 10/2001 | Ambrose et al. |
| 6,337,435 B1 | 1/2002 | Chu et al. |
| 6,406,893 B1 | 6/2002 | Knapp et al. |
| 6,420,143 B1 | 7/2002 | Kopf-sill |
| 6,423,536 B1 | 7/2002 | Javanovich et al. |
| 6,423,948 B1 | 7/2002 | Kwasnoski et al. |
| 6,432,695 B1 | 8/2002 | Lou et al. |
| 6,444,461 B1 | 9/2002 | Knapp et al. |
| 6,448,066 B1 | 9/2002 | Wheatcroft |
| 6,503,750 B1 | 1/2003 | Benett et al. |
| 6,509,186 B1 | 1/2003 | Zou et al. |
| 6,524,532 B1 | 2/2003 | Northrup et al. |
| 6,524,830 B2 | 2/2003 | Kopf-sill |
| 6,537,799 B2 | 3/2003 | Chow et al. |
| 6,541,274 B2 | 4/2003 | Nagle et al. |
| 6,551,841 B1 | 4/2003 | Wilding et al. |
| 6,576,459 B2 | 6/2003 | Miles et al. |
| 6,586,233 B2 | 7/2003 | Benett et al. |
| 6,602,473 B1 | 8/2003 | Northrup et al. |
| 6,605,213 B1 | 8/2003 | Ammann et al. |
| 6,656,724 B1 | 12/2003 | Heimberg et al. |
| 6,657,169 B2 | 12/2003 | Brown et al. |
| 6,660,517 B1 | 12/2003 | Wilding et al. |
| 6,670,153 B2 | 12/2003 | Stern |
| 6,677,151 B2 | 1/2004 | Sandell |
| 6,699,713 B2 | 3/2004 | Benett et al. |
| 6,703,236 B2 | 3/2004 | Atwood et al. |
| 6,756,019 B1 | 6/2004 | Dubrow et al. |
| 6,762,049 B2 | 7/2004 | Zou et al. |
| 6,767,512 B1 | 7/2004 | Lurz et al. |
| 6,814,934 B1 | 11/2004 | Higuchi |
| 6,830,936 B2 | 12/2004 | Anderson et al. |
| 6,875,602 B2 | 4/2005 | Gutierrez |
| 6,962,821 B2 | 11/2005 | Danssaert et al. |
| 7,005,617 B2 | 2/2006 | Brown |
| 7,008,789 B2 | 3/2006 | Gambini et al. |
| 7,030,340 B2 | 4/2006 | Knoche |
| 7,051,536 B1 | 5/2006 | Cohen et al. |
| 7,074,367 B2 | 7/2006 | Lurz et al. |
| 7,133,726 B1 | 11/2006 | Atwood et al. |
| 7,164,077 B2 | 1/2007 | Venkatasubramaniam |
| 7,183,103 B2 | 3/2007 | Gambini et al. |
| 7,238,321 B2 | 7/2007 | Wittwer et al. |
| 7,311,794 B2 | 12/2007 | Joseph et al. |
| 7,417,726 B2 | 8/2008 | Kao et al. |
| 7,429,479 B2 | 9/2008 | Harding et al. |
| 7,460,223 B2 | 12/2008 | Harding et al. |
| 7,504,241 B2 | 3/2009 | Atwood et al. |
| 7,560,273 B2 | 7/2009 | Sandell |
| 7,611,674 B2 | 11/2009 | Heimberg et al. |
| 7,771,933 B2 | 8/2010 | Arciniegas et al. |
| 9,132,427 B2 | 9/2015 | Joseph et al. |
| 9,828,576 B2 | 11/2017 | Viasnoff et al. |
| 2001/0055765 A1 | 12/2001 | O'keefe et al. |
| 2002/0030044 A1 | 3/2002 | Brown |
| 2002/0060156 A1 | 5/2002 | Mathies et al. |
| 2002/0068357 A1 | 6/2002 | Mathies et al. |
| 2002/0072112 A1 | 6/2002 | Atwood et al. |
| 2002/0072113 A1 | 6/2002 | Barbera-Guillem et al. |
| 2002/0110899 A1 | 8/2002 | Wheatcroft |
| 2002/0127660 A1 | 9/2002 | Danssaert |
| 2002/0144771 A1 | 10/2002 | Kuczynski |
| 2002/0182544 A1 | 12/2002 | Chan-Park et al. |
| 2003/0006003 A1 | 1/2003 | Matsuoka |
| 2003/0008286 A1 | 1/2003 | Zou et al. |
| 2003/0040011 A1 | 2/2003 | Barth et al. |
| 2003/0040104 A1 | 7/2003 | Barbera-Guillem et al. |
| 2003/0138829 A1 | 7/2003 | Unger et al. |
| 2003/0138941 A1 | 7/2003 | Gong et al. |
| 2003/0157509 A1 | 8/2003 | Mirzabekov et al. |
| 2003/0199081 A1 | 10/2003 | Wilding et al. |
| 2003/0214994 A1 | 11/2003 | Schicke et al. |
| 2004/0018610 A1 | 1/2004 | Sandell |
| 2004/0029303 A1 | 2/2004 | Hart et al. |
| 2004/0072334 A1 | 4/2004 | Benett et al. |
| 2004/0096958 A1 | 5/2004 | Pottathil et al. |
| 2004/0185504 A1 | 9/2004 | Pantoliano et al. |
| 2004/0209331 A1 | 10/2004 | Ririe |
| 2004/0258568 A1 | 12/2004 | Lurz et al. |
| 2005/0019792 A1 | 1/2005 | McBride et al. |
| 2005/0112634 A1 | 5/2005 | Woudenberg et al. |
| 2005/0129581 A1 | 6/2005 | McBride et al. |
| 2005/0145273 A1 | 7/2005 | Atwood et al. |
| 2005/0176155 A1 | 8/2005 | Klein et al. |
| 2005/0225751 A1 | 10/2005 | Sandell et al. |
| 2005/0233324 A1 | 10/2005 | Corbett et al. |
| 2006/0027317 A1 | 2/2006 | Joseph et al. |
| 2006/0030035 A1 | 2/2006 | Joseph et al. |
| 2006/0030036 A1 | 2/2006 | Joseph et al. |
| 2006/0030037 A1 | 2/2006 | Joseph et al. |
| 2006/0046304 A1 | 3/2006 | Shigeura et al. |
| 2006/0073491 A1 | 4/2006 | Joseph et al. |
| 2006/0088931 A1 | 4/2006 | Ririe |
| 2006/0094108 A1 | 5/2006 | Yoder |
| 2006/0166226 A1 | 7/2006 | Kudoh et al. |
| 2006/0205064 A1 | 9/2006 | Tajima |
| 2006/0246493 A1 | 11/2006 | Jensen et al. |
| 2006/0270026 A1 | 11/2006 | Soh et al. |
| 2007/0084279 A1 | 4/2007 | Huang et al. |
| 2007/0290282 A1 | 12/2007 | Belov et al. |
| 2008/0026483 A1 | 1/2008 | Oldenburg |
| 2008/0288179 A1 | 11/2008 | Kao et al. |
| 2008/0299651 A1 | 12/2008 | Atwood et al. |
| 2010/0233698 A1 | 9/2010 | Joseph et al. |

FOREIGN PATENT DOCUMENTS

| | | | |
|---|---|---|---|
| EP | 0733098 B1 | 1/2006 | |
| EP | 1539353 B1 | 2/2006 | |
| EP | 1510823 A3 | 7/2006 | |
| GB | 2370112 A | 6/2002 | |
| JP | 2002-010777 A | 1/2002 | |
| JP | 2003-014753 A1 | 1/2003 | |
| JP | 2003-107094 A | 4/2003 | |
| JP | 2006-223309 A | 8/2006 | |
| WO | 96/15269 A2 | 5/1996 | |
| WO | WO 9615269 A2 * | 5/1996 | ............ B01D 61/18 |
| WO | 199742500 | 11/1997 | |
| WO | 2005028109 A2 | 3/2002 | |
| WO | 2001009389 | 2/2003 | |
| WO | 2005028110 A2 | 3/2005 | |
| WO | 2005028109 A3 | 7/2005 | |
| WO | 2005028110 A3 | 8/2005 | |
| WO | 2005108604 A2 | 11/2005 | |
| WO | 2005028629 A3 | 6/2006 | |
| WO | 2006/102264 A1 | 9/2006 | |
| WO | 2006102264 A1 | 9/2006 | |
| WO | WO 2006102264 A1 * | 9/2006 | ............ B01L 3/5025 |
| WO | 2009083648 A2 | 7/2009 | |
| WO | 2009100933 A1 | 8/2009 | |
| WO | 2009083648 A3 | 9/2009 | |
| WO | 2010140982 A1 | 12/2010 | |

OTHER PUBLICATIONS

International Search Report dated Nov. 18, 2005 for PCT Application No. PCT/US2005/018297.

International Search Report dated Jun. 11, 2008 for PCT Application No. PCT/US2008/000860.

Yoon et al., "Precise temperature and rapid thermal cycling in a micromachined DNA polymerase chain reaction chip." J. Micromech. Microeng. 2002, 12:813-823.

Beier et al., "Versatile derivatisation of solid support media for covalent bonding on DNA-microchips." Nucleic Acids Res. May 1, 1999;27(9)1970-7.

Guschin et al., "Manual manufacturing of oligonucleotide, DNA, and protein microchips." Anal Biochem. Aug. 1, 1997; 250(2):203-11.

(56) References Cited

OTHER PUBLICATIONS

Innis et al., Optimization of PCRs. In: PCR Protocols (Innis, Gelfand, Sninsky and White, eds.) Academic Press, New York. 1990; pp. 3-12.
Joos et al., "Covalent attachment of hybridizable oligonucleotides to glass supports." Anal Biochem. Apr. 5, 1997;247(1):96-101.
McPherson et al. eds. The Series Methods in Enzymology (Academic Press, Inc.): PCR 2: A Practical Approach. Oxford University Press. New York 1995. (Cover pages and tables of contents only).
Methods in Molecular Biology vol. 20 (1993) (Cover pages and table of contents only).
Quirk et al., Semiconductor Manufacturing Technology. Prentice Hall, NJ. 2001 (55 pages).
Rychlick et al., "Optimization of the annealing temperature for DNA amplification in vitro." Nucleic Acids Res. Nov. 11, 1990; 18(21):6409-12.
Sambrook et al., Molecular Cloning: A Laboratory Manual, 2nd edition (1989).
Wolf, S. Silicon Processing for the VLSI Era. vols. 1-4. Lattice Press 2002.
Nagai et al., "High-throughput PCR in silicon based microchamber array." Biosensors & Bioelectrics 2001 16:1015-1019.

\* cited by examiner

APPARATUS FOR HIGH THROUGHPUT CHEMICAL REACTIONS

CROSS-REFERENCE

This application is a continuation of U.S. patent application Ser. No. 13/594,562, filed Aug. 24, 2012, which is a divisional of U.S. patent application Ser. No. 12/009,953, filed on Jan. 22, 2008, now U.S. Pat. No. 8,252,581, which claims the benefit of U.S. Provisional Application No. 60/886,067, filed Jan. 22, 2007 and U.S. Provisional Application No. 61/016,377, filed Dec. 21, 2007, which applications are incorporated herein by reference in their entirety.

BACKGROUND OF THE INVENTION

The advent and development of Polymerase Chain Reaction (PCR) since 1983 has revolutionized molecular biology through vastly extending the capability to identify, manipulate, and reproduce DNA. A number of different applications have been developed to utilize PCR, such as scientific research, clinical diagnostics, forensic identifications, and environmental studies.

Following the sequencing of the human genome, genomic analysis of the estimated 30,000 human genes has been a major focus of basic and applied biochemical and pharmaceutical research. Diagnostics, medicines, and therapies for a variety of disorders may be developed from the analysis and manipulation of genes. Diagnostic devices often utilize small samples from patients. Patient samples collected for diagnostic purposes are typically of limited quantity and volume and thus only a small number of tests can be performed on a single sample. Therefore, there is need for a miniaturized device capable of performing analysis of a large number of genes or nucleic acid sequences from a single small sample.

Development of gene-based therapies has also become a major focus for both researchers and pharmaceuticals. In order to develop new therapies and recognize new therapeutic targets, high-throughput screening utilizing most, if not all, of an entire genome of an organism would be desirable. In addition, the ability to sequence and amplify an entire genome from a sample from an individual may pave the way for the development of personal medicines.

Many of the PCR microplates and thermocyclers currently available are unable to performing a large quantity of PCR at a reasonable cost. In many reactions, the sample volume needed to analyze each individual sequence is on the order of microliters. When sequencing or amplifying thousands of genes, the amount of sample needed from an individual or group of individuals often becomes not practical. In addition, when dealing with a large number of sequences, the sensitivity and specificity of the reactions become a major issue when performing PCR. The annealing temperatures necessary for PCR amplification of a sequence can vary by as much as 15° C. from sequence to sequence. In order to sequence thousands of genes from a relatively small sample, a thermal cycling apparatus needs to adapt to range of different temperatures.

In recent years, the advancement in nanofabrication technology enabled the production of miniaturized devices integrated with electrical, optical, chemical or mechanical elements. The technology embodies a range of fabrication techniques including low-pressure vapor deposition, photolithography, and etching. Based on these techniques, miniaturized devices containing silicon channels coupled to nano-heaters have been proposed (see, for example, U.S. Pat. Nos. 6,962,821, 6,054,263, 5,779,981 and 5,525,300). While the channel- or chamber-based design in principle reduces the thermal mass and the reaction volume, it still suffers from other practical drawbacks. In particular, the channels or chambers by design are limited with respect to controlling temperature and evaporation.

Such devices or systems would greatly aid in diagnostic testing, pharmaceutical development, and personal medicine. The present invention satisfies this need and provides related advantages as well.

SUMMARY OF THE INVENTION

In general in one aspect an apparatus is provided comprising at least one heating element, configured to be in thermal contact with a chip said chip comprising a substrate and an array of nanowells, wherein the at least one heating element is configured to move relative to the chip.

In one embodiment heating element is in thermal contact with the chip from above and below the chip, and wherein the heating element in thermal contact from below the chip is set at a temperature lower than the temperature of the heating element in thermal contact from above the chip. In another embodiment the chip comprises an upper surface and a bottom surface and wherein a first series of nanowells is arranged along one orientation on the upper surface and a second series of nanowells is oriented perpendicular to the first series of nanowells. The heating element can be positioned above or below a stationary chip comprising an array of nanowells and the heating element can be capable of heating and cooling.

In one embodiment the apparatus includes a plurality of heating elements corresponding to a plurality of temperature zones. The plurality of temperature zones can be within a range from about 52° C. to about 95° C. In another embodiment the plurality of temperature zones provides a temperature gradient. The at least one of the temperature zones can be set at a temperature ranging from about 52° C. to about 65° C. and at least one other temperature zone can be set at a temperature ranging from about 90° C. to about 95° C. In a further embodiment at least one other temperature zone set at an elongation temperature ranging from about 68° C. to about 72° C.

In a particular embodiment the at least one heating element is configured to provide an output comprising a spike waveform of temperature over time.

In one embodiment an individual nanowell in said array has a dimension of about 250 µm in length, about 250 µm in width, and a depth of about 525 µm, or less.

In another embodiment the chip is operatively coupled to an optical system that detects optical signals. The optical system can comprise a plurality of optical detectors.

In one embodiment the number of nanowells is greater than about 30,000. In another embodiment the nanowells are configured to contain about 100 nl.

In general in another aspect a method of conducting a chemical reaction is provided comprising providing a chip configured to receive a reaction sample; providing at least one heating element positionable in relation to the chip to provide thermal contact between the at least one heating element and the chip; and conducting the chemical reaction in the reaction sample by varying the temperature of the chip, wherein said varying the temperature is effected by moving the at least one heating element in relation to the chip such that the heating element is in thermal contact with the chip.

In one embodiment the chemical reaction is a nucleic acid amplification reaction.

In another embodiment movement of the at least one heating element is controlled by signals generated from a temperature sensor that is operatively linked to the chip.

In a further embodiment the reaction sample is capable of producing an optical signal, and, wherein the chip is operatively coupled to an optical system configured to detect optical signals emitted from the reaction sample. The optical signals can be proportional to the amount of product of the chemical reaction.

In one embodiment varying the temperature is effected by moving a plurality of heating elements, each of which is set at a different temperature. In another embodiment at least one heating element is set at a temperature ranging from about 52° C. to about 65° C. and at least one other heating element is set at a temperature ranging from about 90° C. to about 95° C.

In general in another aspect a chip for running a reaction is provided comprising an array of addressable units, each unit being configured for a chemical reaction, wherein the array of the addressable units is configured to correspond to a predetermined temperature zone, and wherein an individual unit in said array is dimensioned to hold a chemical reaction mixture of less than about 1 µl. In one embodiment the apparatus is comprising a plurality of arrays. In another embodiment the apparatus includes a plurality of arrays, each of which corresponding to a different temperature zone. In one embodiment at least one of the arrays is set at an annealing temperature for supporting a nucleic acid amplification reaction and at least one other array is set at a denaturing temperature for supporting a nucleic acid amplification reaction.

In a particular embodiment the zone is addressed to indicate the predetermined temperature zones. In another embodiment the array of addressable units are configured to correspond to six or more predetermined temperature zones.

In one embodiment the chip is in thermal contact with a heating element.

In general in another aspect an apparatus is provided for conducting a chemical reaction requiring cycling at least two temperature levels, comprising: (a) chip for running a reaction comprising an array of addressable units, each unit being configured for a chemical reaction, wherein the array of the addressable units is configured to correspond to a predetermined temperature zone, and wherein an individual unit in said array is dimensioned to hold a chemical reaction mixture of less than about 1 µl; and (b) a heating element in thermal contact with the chip.

In one embodiment the array of addressable units is greater than about 30,000.

In a particular embodiment the apparatus is further comprising (c) an optical system operatively coupled to the chip, wherein the optical system detects an optical signal coming from an addressed thermo-controllable unit. In one embodiment the optical system comprises a plurality of optical detectors.

In one embodiment the apparatus is further comprising a plurality of heating elements. In a particular embodiment the plurality of heating elements comprises six or more heating elements. In one embodiment an individual unit within the array comprises a nanowell for receiving and confining a sample, said well being sealed when filled with the sample. In another embodiment the chemical reaction is a nucleic acid amplification reaction. In one embodiment the predetermined temperature of a unit is configured to yield at least 90% of homogeneous product from the chemical reaction.

In general in another aspect a method of conducting a reaction that involves a plurality of reaction simples and requires cycling at least two temperature levels is provided comprising: (a) providing a chip for running a reaction comprising an array of addressable units, each unit being configured for a chemical reaction, wherein the array of the addressable units is configured to correspond to a predetermined temperature zone, and wherein an individual unit in said array is dimensioned to hold a chemical reaction mixture of less than about 1 µl; (b) placing the plurality of reaction samples into the units of the chip according to the set of predetermined temperatures; and (c) controlling a heating element to effect cycling at least two temperature levels.

In one embodiment an individual unit within the array of the chip comprises a nanowell for receiving and confining a sample, said well being sealed when filled with the sample. In another embodiment the chemical reaction is a nucleic acid amplification reaction. In a further embodiment the predetermined temperature of a unit is configured to yield at least 90% of homogeneous product from the chemical reaction.

In general in yet another aspect an apparatus for conducting a chemical reaction involving cycling at least two temperature levels is provided comprising: (a) a body configured to receive a chip comprising a plurality of nanowells for containing the chemical reaction; and (b) a first heater providing a first temperature and a second heater providing a second temperature; wherein the first heater and the second heater are configured to be movable between a first and a second orientation, and wherein the first orientation places the heater in thermal contact with the sample holder and the second orientation does not place the heater in thermal contact with the sample holder.

In one embodiment the plurality of nanowells are addressable, wherein the nanowells are arranged according to a predetermined set of temperatures, such that at least one of the nanowells is addressed td indicate the predetermined temperature for running the chemical reaction within said nanowell. In a particular embodiment the plurality of nanowells comprises over about 30,000 nanowells.

In one embodiment the first heater comprises a plurality of temperature zones. In another embodiment the temperature zones comprise six or more temperature zones. In a further embodiment the plurality of temperature zones correspond to the predetermined set of temperatures according to which the thermo-controllable units are arrayed. In one embodiment the first and second heaters move between the first and second orientations according to a protocol.

In a further embodiment the apparatus is comprising a motor for moving the first and second heaters between the first and second orientations.

In one embodiment the first heater can provide a temperature gradient. In another embodiment the apparatus is further comprising a heat sink in thermal contact with the first heater. In a different embodiment the apparatus is further comprising a heat sink in thermal contact with the second heater.

In some embodiments the apparatus is further comprising a fan for removing heat from the heat sink. In other embodiments the apparatus is further comprising a plurality of temperature sensors operably connected to the chip. In one embodiment the plurality of temperature sensors has at least one temperature sensor assigned to measure the temperature of each temperature zone.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
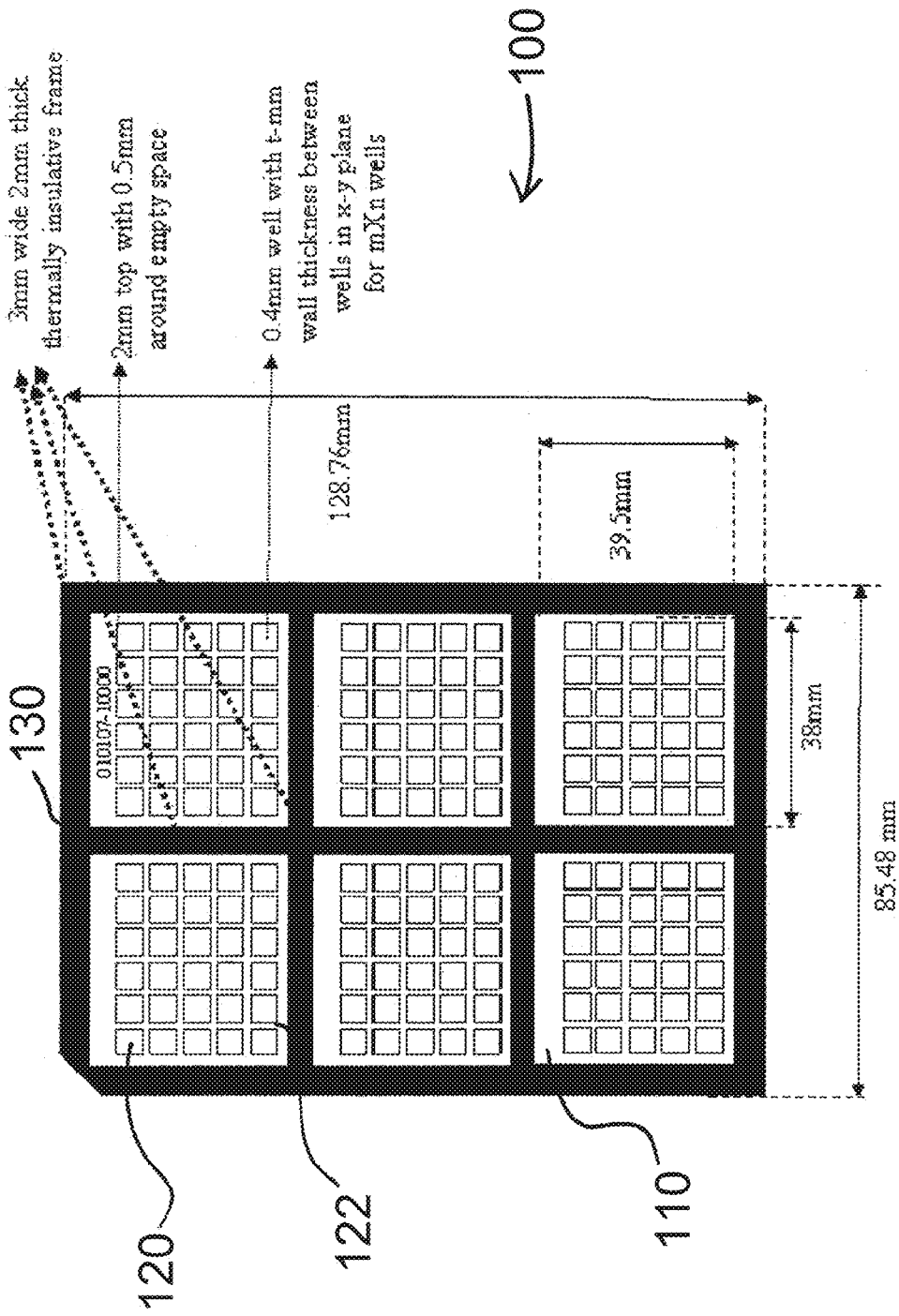
FIG. 1 illustrates an exemplary embodiment of a chip of the invention that comprises six smaller chips or six arrays of addressable units representing different addressed predetermined temperatures.

The present invention provides chips, thermal cycling apparatuses, systems, and methods for conducting a plurality of chemical reactions and for multiplexed analyses of individual molecules. The present invention also provides miniaturized, highly automated devices and methods that allow the manipulation of the precise control of the reaction substance, conditions and temperature.

The present invention can relate to methods, chips, and apparatuses for simultaneously analyzing a whole genome of an organism. Many of the methods relate to the qualitative and/or quantitative analysis of a genomic mixture of nucleotides, using polymerase chain reaction or similar amplification methods conducted in very small reaction volumes.

The analysis of the estimated 30,000 human genes may provide methods for applied pharmaceutical research and developing diagnostics, medicines and therapies for wide variety of disorders. For example, through understanding of genetic differences between normal and diseased individuals, differences in the biochemical makeup and function of cells and tissues can be determined and appropriate therapeutic interventions identified.

In an embodiment, the genome may be from humans, mammals, mice, *Arabidopsis* or any other plant, bacteria, fungi or animal species. The invention may be used for drug discovery and for diagnostics of a particular individual, animal or plant.

In many situations, it can be desirable to determine the gene expression profile from a test of all genes in an organism. Such a test can also be useful to screen DNA or RNA from a single individual for sequence variants associated with different mutations in the same or different genes (for example, single nucleotide polymorphisms, or "SNPs"), or for sequence variants that serve as markers for the inheritance of different chromosomal segments from a parent. Such tests can also be useful, for example, to predict susceptibility to disease, determine whether an individual is a carrier of a genetic mutation, determine whether an individual may be susceptible to adverse reactions or resistance to certain drugs, or for other diagnostic, therapeutic or research purposes.

Chips

The overall size of a chip of the invention may vary and it can range from a few microns to a few centimeters in thickness, and from a few millimeters to 50 centimeters in width or length. Typically, the size of the entire chip ranges from about 10 mm to about 200 mm in width and/or length, and about 1 mm to about 10 mm in thickness. In some embodiments, the chip is about 40 mm in width by 40 mm in length by 3 mm in thickness.

The chip can also be a set of smaller chips. For example, the chip can comprise six smaller chips (e.g., six arrays of addressable units) with a thermal buffer between each of the smaller chips. A chip that is a set of smaller chips is also referred to herein as a plate. In an embodiment of the example, each of the six smaller chips corresponds to a different predetermined temperature to which the array of units in the overall chip are addressed.

The total number of units on the chip will vary depending on the particular application in which the subject chips are to be employed. The density of the units on the chip surface may vary depending on the particular application. The density of units (for example, number of chambers per unit surface area of substrate), and the size and volume of units, may vary depending on the desired application and such factors as, for example, the species of the organism for which the methods of this invention are to be employed.

A large number of units may be incorporated into a chip of the invention. In various embodiments, the total number of units on the chip is from about 1000 to about 200,000, more preferably from about 5000 to about 100,000. In other embodiments the chip comprises smaller chips, each of which comprises about 5,000 to about 20,000 units. Therefore, if the larger chip comprises about 3 to about 20 smaller chips, it comprises about 15,000 to about 400,000 units. In certain embodiments, the chip comprises about 100,000 units.

For example, a square chip may comprise 125 by 125 nanowells, with a diameter of 0.1 mm. Table I shows some examples of the well layout format for certain exemplary chips of the invention. A plate is equivalent to a chip comprising multiple smaller chips as described herein. In the example of Table I, a plate comprises six smaller chips.

TABLE I

| m (approx.) | n (approx.) | depth (mm) | ~Wells/Chip (approx.) | Wells/plate (approx.) |
| --- | --- | --- | --- | --- |
| 125 | 125 | 0.1 | 15743 | 94459 |
| 122 | 122 | 0.11 | 14790 | 88742 |
| 118 | 118 | 0.12 | 13921 | 83527 |
| 115 | 115 | 0.13 | 13126 | 78756 |
| 111 | 111 | 0.14 | 12397 | 74381 |
| 108 | 108 | 0.15 | 11726 | 70358 |
| 105 | 105 | 0.16 | 11108 | 66651 |
| 103 | 103 | 0.17 | 10538 | 63228 |
| 100 | 100 | 0.18 | 10010 | 60060 |
| 98 | 98 | 0.19 | 9521 | 57124 |
| 95 | 95 | 0.2 | 9066 | 54396 |
| 93 | 93 | 0.21 | 8643 | 51858 |
| 91 | 91 | 0.22 | 8249 | 49492 |
| 89 | 89 | 0.23 | 7881 | 47283 |
| 87 | 87 | 0.24 | 7536 | 45218 |
| 85 | 85 | 0.25 | 7214 | 43285 |
| 83 | 83 | 0.26 | 6912 | 41472 |

In Table I m is an approximate number of wells along a horizontal axis, n is an approximate number of wells along a perpendicular axis, depth is measured in mm, and the number of wells/chip and number of wells/plate are approximate.

The chip can be of any size or have any number of units. In an embodiment, a user or a customer receiving a chip of the invention chooses the size, units and whether a unit comprises a nanowell. In a preferable embodiment, when running a nucleic acid amplification chemical reaction with a unit on a chip of the invention, the user can select the number of units according to the number of genes required to sequence an entire genome of a species.

An example chip 100 of the embodiment comprising six smaller chips 110 is illustrated in FIG. 1. The smaller chips 110 are 38 mm by 39.5 mm in area, and the overall size of the chip 100 comprising the six smaller chips 110 is about 85 mm by 129 mm in area. In this example, the smaller chips 110 comprise a large well size of about 400 µm (not represented in scale in the figure). The smaller chips 110 can comprise a series of m by n nanowells 120 as demonstrated in Table I. In this embodiment, the t-mm wall thickness 122 can determine the number of nanowells on a chip. Each of the smaller chips 110 can represent a predetermined temperature of the overall chip 100 and thus, each smaller chip 110 can be addressed according to the temperature of the reaction to be run in each nanowell 120. In addition, when a plurality of smaller chips 110 are used in an overall larger chip 100, a thermally insulative frame 130 can thermally isolate each addressable predetermined temperature area from one another. In this example, the thermally insulative frame 130 is 3 mm in thickness and can be made of mica, polyethylene, or any other insulative material as would be obvious to one skilled in the art.

In an embodiment, a chip can run 33,750 assays for whole genome, high throughput gene expression real-time PCR.

The nanowell may be fabricated in any convenient size, shape or volume. The well may be about 100 µm to about 1 mm in length, about 100 µm to about 1 mm in width, and about 100 µm to about 1 mm in depth. In various embodiments, each nanowell has an aspect ratio (ratio of depth to width) of from about 1 to about 4. In one embodiment, each nanowell has an aspect ratio of about 2. The transverse sectional area may be circular, elliptical, oval, conical, rectangular, triangular, polyhedral, or in any other shape. The transverse area at any given depth of the well may also vary in size and shape.

In an embodiment, the nanowell can have a volume of from about 1 nl to about 1 ul. The nanowell typically has a volume of less than 1 ul, preferably less than 500 nl. The volume may be less than 200 nl, or even less than 100 nl. In an embodiment, the volume of the nanowell is about 100 nl. Where desired, the nanowell can be fabricated to increase the surface area to volume ratio, thereby facilitating heat transfer through the unit, which can reduce the ramp time of a thermal cycle.

The cavity of each nanowell may take a variety of configurations. For instance, the cavity within a nanowell may be divided by linear or curved walls to form separate but adjacent compartments, or by circular walls to form inner and outer annular compartments.

A nanowell of high inner surface to volume ratio may be coated with materials to reduce the possibility that the reactants contained therein may interact with the inner surfaces of the well. Coating is particularly useful if the reagents are prone to interact or adhere to the inner surfaces undesirably. Depending on the properties of the reactants, hydrophobic or hydrophilic coatings may be selected. A variety of appropriate coating materials are available in the art. Some of the materials may covalently adhere to the surface, others may attach to the surface via non-covalent interactions. Non-limiting examples of coating materials include silanization reagent such as dimethychlorosilane, dimethydichlorosilane, hexamethyldisilazane or trimethylchlorosilane, polymaleimide, and siliconizing reagents such as silicon oxide, Aquasil™, and Surfasil™. Additional suitable coating materials are blocking agents such as amino acids, or polymers including but not limited to polyvinylpyrrolidone, polyadenylic acid and polymaleimide.

Certain coating materials can be cross-linked to the surface via extensive heating, radiation, and by chemical reactions. Those skilled in the art will know of other suitable means for coating a nanowell of a chip, or will be able to ascertain such, without undue experimentation.

In an embodiment, an individual unit of the chip comprises a nanowell for receiving and confining a sample, said well being sealed when filled with the sample.

The individual units within the array can be separated from each other by a physical barrier resistant to the passage of liquids. In one aspect, these units may comprise indented areas referred to as nanowells. A nanowell can be open at the top, but is physically isolated from other wells to restrict passage of liquids. Accordingly, the nanowell has at least one cavity suitable for receiving and confining reaction sample. In order to isolate one nanowell from the environment to restrict the passage of liquids, the nanowell can be sealed. In a preferable embodiment, a method of sealing a nanowell is depositing mineral oil on top of the sample within the well to confine the sample. The mineral oil can be nano-dispensed. A nanowell can be sealed by any method as would be obvious to those skilled in the art.

In many applications, sealing nanowells is desirable to prevent evaporation of liquids and thus maintains the preferred reaction concentrations throughout the thermal cycling. Accordingly, a technique for sealing an array of nanowells can be employed. A useful sealing technique takes several factors into consideration. First, the method should be amenable to high throughput processing of a large quantity of nanowells. Second, the method should permit selective sealing of individual nanowells. As such, the method can yield chips comprising open nanowells interspersed among sealed nanowells in any desired pattern or format. An open and/or unfilled well can not only allow passive dissipation of heat, but also can reduce heat transfer between the neighboring nanowells.

An alternative method of sealing results in an array of nanowells containing at least one open well. The method can include the steps of (a) applying a radiation-curable adhesive along peripheral dimensions defining the open surface of the at least one open nanowell; (b) placing a cover to encompass the peripheral dimensions that define the open surface of the at least one open nanowell that is to be sealed; and (c) exposing the array to a radiation beam to effect the sealing.

As used herein, "radiation-curable adhesive" refers to any composition that cures and bonds to the adhering surface upon exposure to a radiation beam without the need of extensive heating. "Radiation beam" refers to electromagnetic waves of energy including, in an ascending order of frequency, infrared radiation, visible light, ultraviolet (UV) light, X-rays, and gamma rays. A vast number of radiation-curable adhesive are commercially available (see, for example, a list of companies selling radiation-curable adhesive and radiation systems from ThomasNet®'s worldwide web site). Such materials include a diversity of acrylics, acrylates, polyurethanes (PUR), polyesters, vinyl, vinyl esters, and a vast number of epoxies that are curable by radiation beams at various frequencies. These and other radiation-curable materials are supplied commercially in form of liquid, or solid such as paste, powder, resin, and tape.

The choice of "radiation-curable adhesive" will be dependent on the material make up of the surfaces to be adhered. The aforementioned classes of adhesive are suited for adhering the chip substrate to the cover which can be made of a range of materials. For instance, acrylics and epoxies are applicable for radiation-sealing any two surfaces, made of any one of the materials selected from glass, ceramics, metalloids, semiconductors (for example, silicon, silicates, silicon nitride, silicon dioxide, quartz, and gallium arsenide), plastics, and other organic polymeric materials. Radiation-curable materials exhibiting the properties of low use temperature and rapid curing time can be desirable for sealing the subject chips. These materials allow for a rapid sealing to avoid radiation damages to the chemical or biological reagents contained in the chips.

The radiation-curable adhesive can be applied by any mechanical means along the peripheral dimensions that define the open surface of a nanowell. The "peripheral dimensions" can be the boundaries on the chip substrate or on the cover. In either case, the peripheral dimensions become bonded to the respective adhering surface, the substrate or the cover, upon curing the adhesive. The radiation-curable adhesive can be smeared, printed, dispensed, or sprayed onto the peripheral dimensions using any suitable tools. Mechanical means can yield a uniform layer of adhesive on the peripheral dimensions. One way to provide a uniform distribution is to apply the adhesive directly onto the peripheral dimensions of an open well using a squeegee over a meshed screen mask. Alternatively, the radiation-curable adhesive can be applied directly onto the cover that has been marked with the peripheral dimensions using the meshed screen mask. A uniform layer of adhesive is achieved upon removal of the mask.

Upon application of the radiation-curable adhesive, a cover is placed on the nanowell to encompass the peripheral dimensions that define the open surface of the well. Suitable covers are generally made of materials that permit passage of a radiation beam. Preferred covers are fabricated with transparent materials such as glass, quartz, plastic, any suitable organic polymeric materials known to those skilled in the art, or any combinations thereof.

Sealing a covered nanowell can be carried out by exposing the well to a radiation beam. Depending on the type of adhesive selected, the radiation beam may come from a conventional incandescent source, a laser, a laser diode, UV-bulb, an X-ray machine or gamma-ray machine, or the like. Where desired, radiation beam from the radiation source is permitted to reach only selected locations on the nanowell array so that only certain selected wells are to be sealed. A selective sealing is often achieved by using a photo-mask patterned with the locations of the nanowells. The photo-mask is provided with transparent locations and opaque locations that correspond to the nanowells that are to be sealed and those that are to remain open, respectively. The radiation beam passes freely through the transparent regions but is reflected from or absorbed by the opaque regions. Therefore, only selected nanowells are exposed to light and hence sealed by curing the adhesive. The photo-mask can be patterned such that no two adjoining open nanowells are to be sealed. The photo-mask can be patterned such that the resulting nanowell array contains alternating sealed and unsealed wells. One skilled in the art can fashion an unlimited number of photo-masks with any patterns to yield chips containing open and sealed nanowells in any format. Methods for manufacturing such photo-masks are well established in the art and hence are not detailed herein.

Figure 2:
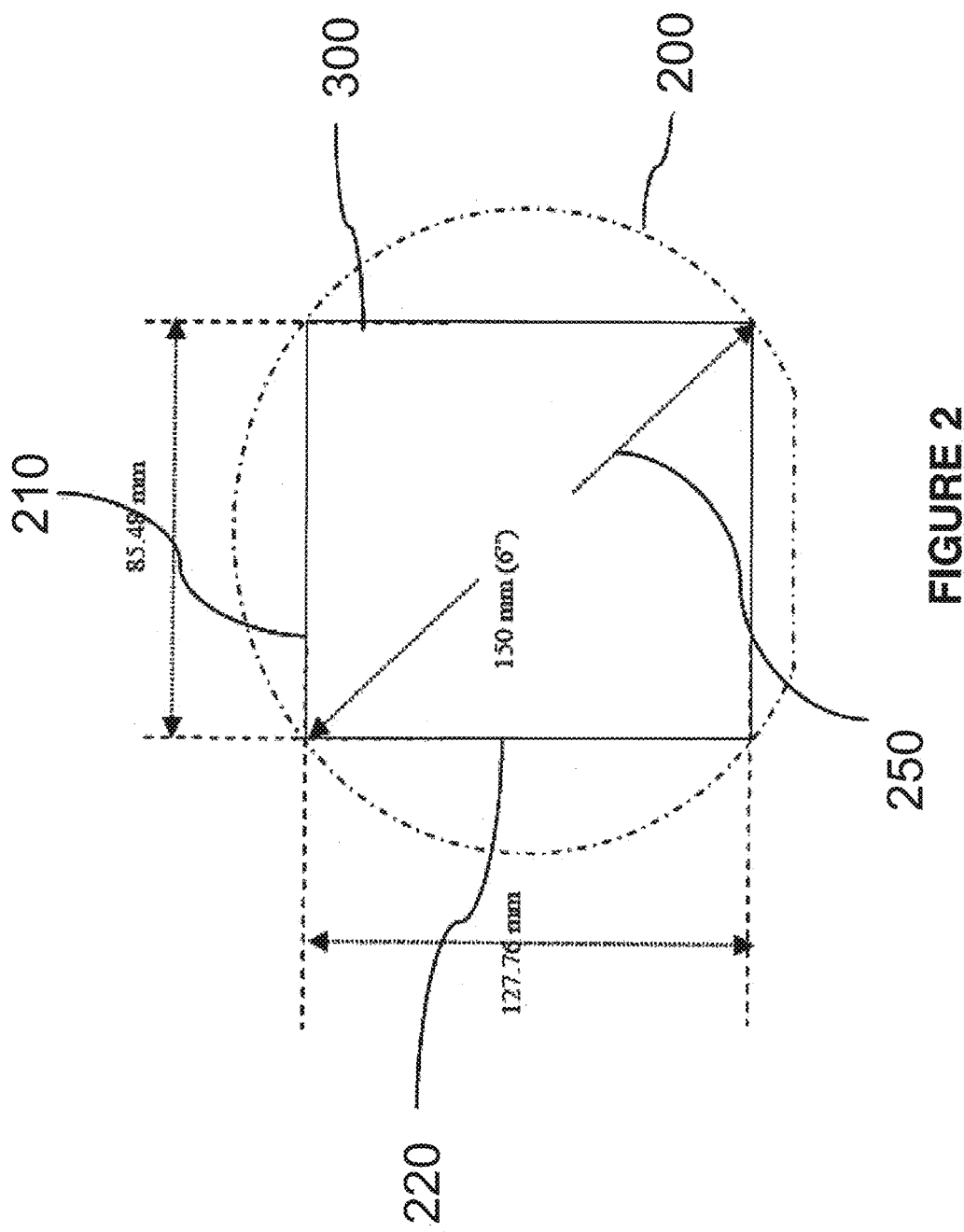
FIG. 2 is a top view of one exemplary chip layout on a circular substrate.

FIG. 2 is a representative schematic drawing of an alternative chip 300 made from a silicon wafer 200. Preferred silicon chips have an overall size of about 500 microns in thickness and may have any width or length depending on the number of nanowells desired. Such a silicon wafer 200 is 6 inches (150 mm) in diameter and 626 µm thick. A chip 300 can be fabricated from such a wafer 200, such chip being approximately 85.48 mm along one side 210, 127.76 mm along the other side 220, and 150 mm along the diagonal length of the chip 250. As fabricated, the chip is an SBS compliant qPCR chip. The total number of nanowells fabricated on the chip will vary depending on the particular application in which the subject chips are to be employed. To accommodate the need for simultaneous performance of a vast number of reactions, the subject chips will generally comprise at least 100 nanowells, and more usually over 30,000 nanowells. The density of the nanowells on the chip surface may vary depending on the particular application. For example, the density of nanowells on the chip surface can range between about 1 to about 1000 nanowells per $mm^2$. In another example the density of nanowells on the chip can range between about 10 to about 100 nanowells per $mm^2$.

Figure 3:
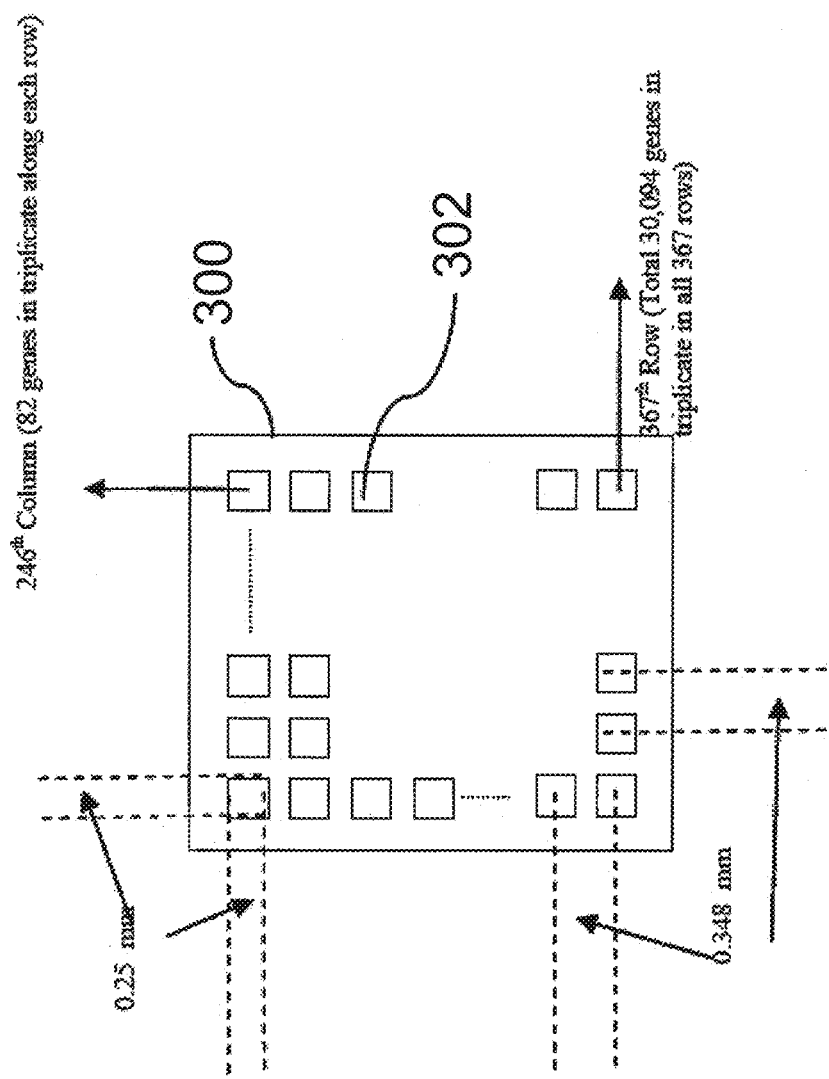
FIG. 3 is a top view of one exemplary chip layout showing nanowells on the chip.

FIG. 3 is an illustrative diagram of the top side of a chip 300 with representative nanowells 302. In one exemplary embodiment, the nanowells 302 of the chip 300 are 0.25 mm in length and 0.25 mm in width and the centers of the nanowells 302 are spaced 0.348 mm apart. It is envisioned that the centers of the nanowells 302 can be spaced as desired, including, for example between 2 mm and 0.01 mm apart. The nanowells of the subject chips can be arrayed in any format across or over the surface of the chip, such as in rows and columns so as to form a grid, in a particular pattern, and the like as seen in FIG. 3. In a preferred embodiment, the nanowells are arrayed in a format compatible to instrumentation already existing for dispensing reagents and/or reading assays, such that engineering of commercially available fluid handling devices is not required. As in the example in FIG. 3, a chip may have at least 246 nanowells, more preferably at least 367 nanowells, and more preferably at least 45,141 nanowells, and even more preferably, at least 90,282 nanowells. While the number of nanowells of the chip may be as many as 90,282 or more, it is envisioned that the number of nanowells can usually does not exceed about 1,444,512 nanowells. The number of nanowells on the preferred embodiment of the chip is sufficient to contain 82 genes in triplicate along each column and 30,094 genes in triplicate in all rows. As in one such preferred embodiment the number of wells are sufficient to screen the entire human genome in triplicate. It is envisioned that the number of nanowells on the chip can include adequate reaction wells for amplifying the entire set of expressed genes in other organisms' genomes as well.

Figure 4:
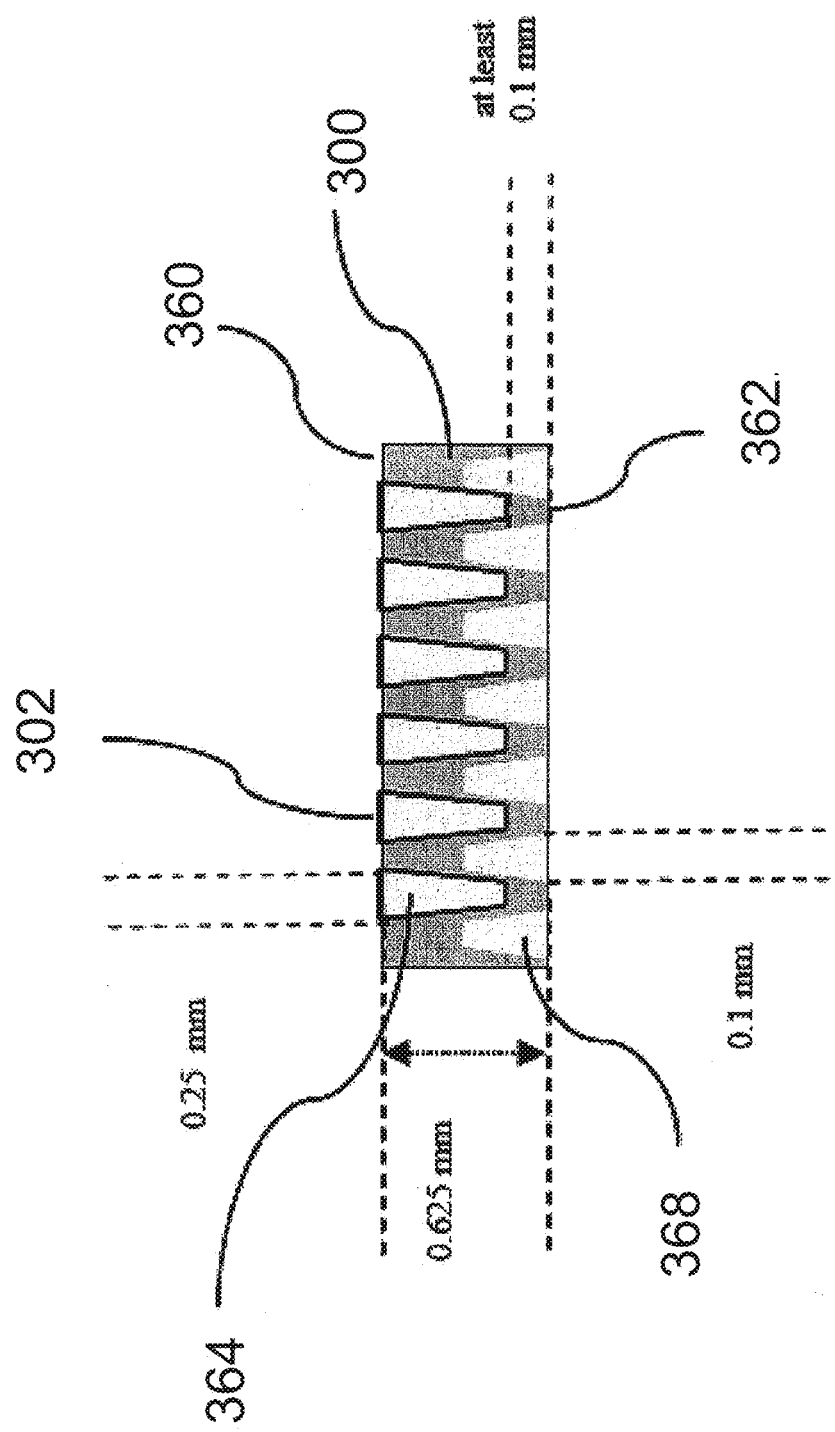
FIG. 4 is a longitudinal cross section of the side view of an exemplary nanowell chip.

FIG. 4 is a cross-sectional side view of second layer of an exemplary chip 300 as shown in FIG. 3. FIG. 4 shows a non-limiting example of a chip 300 with a thickness of 0.625 mm. FIG. 4 also shows the individual well 302 dimensions as being 0.25 mm (250 μm) in length and width. As illustrated, the nanowell depth can be 0.525 mm (525 μm), leaving 0.1 mm of the chip beneath a given well. It is envisioned that nanowell openings can include a shape such as round, square, rectangle or any other desired geometric shape. By way of example, a nanowell can include a diameter or width of between about 100 μm and about 1 mm, a pitch or length of between about 150 μm and about 1 mm and a depth of between about 10 μm to about 1 mm. The cavity of each nanowell make take a variety of configurations. For instance, the cavity within a nanowell may be divided by linear or curved walls to form separate but adjacent compartments.

The nanowells of the chip may be formed using commonly known photolithography techniques. The nanowells may be formed using a wet KOH etching technique or an anisotropic dry etching technique.

A nanowell of high inner surface to volume ration may be coated with materials to reduce the possibility that the reactants contained therein may interact with the inner surfaces of the nanowells. A chip can also be made of resistive heating material. Non-limiting examples of materials include metal plates such as aluminum and stainless steel substrates such as SS-316. Where the substrate used is a metal, it is usually preferable to coat the surface with an insulating layer to prevent corrosion and/or electrophoresis of the sample components during operation with fluid samples. Coating is usually not necessary in the case or non-metal heating material. A variety of protective coatings are available, including those made of, for example, $SiO2$, $Si3N4$, and Teflon. FIG. 4 shows a chip 300 in which the individual wells 302 are etched with KOH and layered with $SiO2$.

FIG. 4 also shows an illustrative chip comprising at least two opposing arrays of nanowells. In this figure, the chip 300 has an upper 360 and a bottom 362 surface. One of the arrays is arranged along the upper surface 364 and the other is arranged in an opposite array along the bottom surface 368. The nanowells of the bottom array are positioned in an inverted manner so that the open surface of each unit points away from that of the opposing unit in the chip. The two opposing arrays may be arranged such that the base of each nanowell is directly opposite to that of the opposing array.

Though not specifically depicted in FIG. 4, any nanowells in the upper 364 and/or bottom 368 arrays may be sealed or unsealed. In addition any nanowell in the upper array may be filled or unfilled, with or without the reaction sample. The subject chip is then placed in thermal contact with a heating element by placing the chip in contact with an external heating element.

The surface of a nanowell of a chip of the invention can further be altered to create adsorption sites for reaction reagents. These sites may comprise linker moieties for attachment of biological or chemical compound such as a simple or complex organic or inorganic molecule, a peptide, a protein (for example antibody) or a polynucleotide. One skilled in the art will appreciate that there are many ways of creating adsorption sites to immobilize chemical or biological reactants. For instance, a wealth of techniques are available for directly immobilizing nucleic acids and amino acids on a chip, anchoring them to a linker moiety, or tethering them to an immobilized moiety, via either covalent or non-covalent bonds (see, for example, Methods Mol. Biol. Vol. 20 (1993), Beier et al., Nucleic Acids Res. 27:1970-1-977 (1999), Joos et al., Anal. Chem. 247:96-101 (1997), Guschin et al., Anal. Biochem. 250:203-211 (1997)). The surface of the nanowell can be plasma etched to allow for immobilization of a probe or primer.

As used herein, the term "chemical reaction" refers to any process involving a change in chemical properties of a substance. Such process includes a vast diversity of reactions involving biological molecules such as proteins, glycoproteins, nucleic acids, lipids, and inorganic chemicals, or any combinations thereof. The subject chips have a wide variety of uses in chemical and biological applications where different temperatures are desired. The chemical reaction may also involve interactions between nucleic acid molecules, between proteins, between nucleic acid and protein, between protein and small molecules. Where the process is catalyzed by an enzyme, it is also referred to as "enzymatic reaction."

The subject chips and other apparatus are particularly useful in conducting enzymatic reactions because most enzymes function under only certain temperatures. Representative enzymatic reactions that are particularly temperature dependent include but are not limited to nucleic acid amplification, such as quantitative polymerase chain reaction (qPCR), nucleic acid sequencing, reverse transcription, and nucleic acid ligation. In an embodiment, a nucleic acid amplification reaction run on a chip of the invention is a real-time polymerase chain reaction. In another embodiment, the nucleic acid amplification reaction is a reverse-transcription coupled polymerase chain reaction.

The chips of the present invention provide a cost-effective means for amplifying nucleic acids. Unlike with conventional microtiter plates and thermal cyclers, the subject chips are highly miniaturized, capable of performing rapid amplification of a vast number of target nucleic acids in small volume, and under independent thermal protocols.

As used herein, "nucleic acid amplification" refers to an enzymatic reaction in which the target nucleic acid is increased in copy number. Such increase may occur in a linear or in an exponential manner. Amplification may be carried out by natural or recombinant DNA polymerases such as Taq polymerase, Pfu polymerase, T7 DNA polymerase, Klenow fragment of *E. coli* DNA polymerase, and/or RNA polymerases such as reverse transcriptase.

In general, the purpose of a polymerase chain reaction (PCR) is to manufacture a large volume of DNA which is identical to an initially supplied small volume of target or seed DNA. The reaction involves copying the strands of the DNA and then using the copies to generate other copies in subsequent cycles. Each cycle will double the amount of DNA present thereby resulting in a geometric progression in the volume of copies of the target DNA strands present in the reaction mixture.

General procedures for PCR are taught in U.S. Pat. No. 4,683,195 (Mullis) and U.S. Pat. No. 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of 2n, where n is the number of cycles.

A typical conventional PCR thermal cycling protocol comprises 30 cycles of (a) denaturation at a range of 90° C. to 95° C., (b) annealing at a temperature ranging from 50° C. to 68° C., and (c) extension at 68° C. to 75° C. With the subject chips, the thermal cycling time can be drastically reduced because of, partly, the small reaction volume, the small heating mass, and the design of effective heat dissipation features.

The subject chips can be employed in reverse transcription PCR reaction (RT-PCR). RT-PCR is another variation of the conventional PCR, in which a reverse transcriptase first coverts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (for example, 30-45° C.) for a sufficient amount of time (for example, 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample. One of skill in the art will appreciate that if a quantitative result is desired, caution must be taken to use a method that maintains or controls for the relative copies of the amplified nucleic acids.

Methods of "quantitative" amplification of nucleic acids are well known to those of skill in the art. For example, quantitative PCR (qPCR) can involve simultaneously co-amplifying a known quantity of a control sequence using the same primers. This provides an internal standard that may be used to calibrate the PCR reaction. Other ways of performing qPCR are available in the art.

Nucleic acid amplification is generally performed with the use of amplification reagents. Amplification reagents typically include enzymes, aqueous buffers, salts, primers, target nucleic acid, and nucleoside triphosphates. Depending upon the context, amplification reagents can be either a complete or incomplete amplification reaction mixture.

Reagents contained within a chip of the invention depend on the reaction that is to be run. In an embodiment, at least one of the units of the array of addressable units contains a reagent for conducting the nucleic acid amplification reaction. Reagents can be reagents for immunoassays, nucleic acid detection assays including but not limited to nucleic acid amplification. Reagents can be in a dry state or a liquid state in a unit of the chip.

In an embodiment; at least one of the units of the array of addressable units of a chip capable of carrying out a nucleic acid amplification reaction contains at least one of the following: a probe, a polymerase, and a dNTP. In another embodiment, the nanowellis of a chip contain a solution comprising a probe, a primer and a polymerase. In various embodiments, each chamber comprises (1) a primer for a polynucleotide target within said standard genome, and (2) a probe associated with said primer which emits a concentration dependent signal if the primer binds with said target.

In various embodiments, each unit comprises a primer for a polynucleotide target within a genome, and a probe associated with the primer which emits a concentration dependent signal if the primer binds with the target.

In another embodiment, at least one unit of the chip contains a solution that comprises a forward PCR primer, a reverse PCR primer, and at least one FAM labeled MGB quenched PCR probe.

In an embodiment, primer pairs are dispensed into a unit and then dried, such as by freezing. The user can then selectively dispense, such as nano-dispense, the sample, probe and/or polymerase.

In other embodiments of the invention, the nanowells may contain any of the above solutions in a dried form. In this embodiment, this dried form may be coated to the wells or be directed to the bottom of the well. The user can add a mixture of water and the sample to each of the wells before analysis.

In this embodiment, the chip comprising the dried down reaction mixture may be sealed with a liner, stored or shipped to another location. The liner is releasable in one piece without damaging the adhesive uniformity. The liner is visibly different than the cover to aid in identification and for ease of handling. The material of the liner is chosen to minimize static charge generation upon release from the adhesive. When the user is ready to use the chip, the seal is broken and the liner is removed and the sample is added to the units of the chip. The chip can then sealed and placed into contact with a heating element.

In many applications, sealing the units (for example, nanowells) is desirable to prevent evaporation of liquids and thus maintains the preferred reaction concentrations throughout the thermal cycling.

The chip may be used for genotyping, gene expression, or other DNA assays preformed by PCR. Assays performed in the plate are not limited to DNA assays such as Taqman, Invader, Taqman Gold, SYBR gold, and SYBR green but also include other assays such as receptor binding, enzyme, and other high throughput screening assays. In some embodiments, a ROX labeled probe is used as an internal standard.

The invention also provides a method for performing a PCR analysis using a chip comprising a plurality of pre-loaded nanowells, the method comprising: placing a sample into the nanowells to create a reaction mixture; sealing the nanowells of the chip with mineral oil or another sealing mechanism; placing the chip into a thermal cycling system; cycling the system; and analyzing results:

In accordance with the present invention, the units of the chip comprise a solution operable to perform multiplex PCR. In a preferable embodiment, the units are capable of having multiple PCR reactions in each individual unit based on the chemistry and the probes that are included in the solution. "Multiplex PCR" is the use of more than one primer pair in the same unit. This method can be used for relative quantitation where one primer pair amplifies the target and another primer pair amplifies the endogenous reference. A multiplex reaction can be performed using a variety of methods including the Standard Curve Method or the Comparative Ct Method.

Various probes can be used, such as FAM which is a carboxy-fluorescein which has an excitation wavelength from about 485 nm and an emission wavelength from about 510-520 nm; SYBR Green 1 which is normally used for RT-PCR and has an excitation wavelength of about 488 nanometers and an emission wavelength of about 510 nanometers; TET which has an emission wavelength from about 517 nanometers to about 538 nanometers; the probes from the group of HEX, JOE and VIC, which have emission wavelengths from 525-535 nm to about 546-556 nm; TAMRA which is a carboxy-tetra methylrhodamine, and has an emission wavelength from about 556 nanometers to about 580 nanometers; ROX which is a carboxy-x-rhodamine, which has an emission wavelength from about 575-585 nm to about 605-610 nm; ALEXA, which has an emission range from about 350 nanometers to about 440 nanometers; TEXAS RED, which has an emission wavelength from about 580-585 nm to about 600-610 nm; Cy3, which has an emission wavelength of about 545 nanometers to about 568 nanometers; Cy5, which has an emission wavelength of about 635-655 nm to about 665-675 nm; Cy7, which has an emission wavelength of about 715 nanometers to about 787 nanometers. Optimized interference filters precisely match the excitation and emission wavelengths for each fluorophore to block out unwanted cross-talk from spectrally adjacent fluorophores.

The choice of primers for use in nucleic acid amplification will depend on the target nucleic acid sequence. Primers used in the present invention are generally oligonucleotides, usually deoxyribonucleotides several nucleotides in length, that can be extended in a template-specific manner by the polymerase chain reaction. The design of suitable primers for amplifying a target nucleic acid can be determined by one skilled in the art.

For a convenient detection of the amplified nucleic acids resulting from PCR or any other nucleic acid amplification reactions described above or known in the art, primers may be conjugated to a detectable label. Detectable labels suitable for use in the present invention include any composition detectable by spectroscopic, photochemical, biochemical, immunochemical, electrical, optical or chemical means. A wide variety of appropriate detectable labels are known in the art, which include luminescent labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The labels may be incorporated by any of a number of means well known to those of skill in the art. In one aspect, the label is simultaneously incorporated during the amplification step. Thus, for example, PCR with labeled primers or labeled nucleotides can provide a labeled amplification product. In a separate aspect, transcription reaction in which RNA is converted into DNA, using a labeled nucleotide (for example fluorescein-labeled UTP and/or CTP) or a labeled primer, incorporates a detectable label into the transcribed nucleic acids.

The invention also provides reagents and kits suitable for carrying out polynucleotide amplification methods of this invention. Such reagents and kits may be modeled after reagents and kits suitable for carrying out conventional PCR, RT-PCR, and other amplification reactions. Such kits comprise a chip of the invention and a reagent selected from the group consisting of an amplification reagent, a detection reagent and combinations thereof. The kits may comprise reagents packaged for downstream or subsequent analysis of the multiplex amplification product. The primers included in the individual units can, independently of one another, be the same or a different set of primers comprising the plurality of multiplex amplification primers.

In another embodiment, the oligonucleotide probes are suitable for detecting single nucleotide polymorphisms, as is well-known in the art. A specific example of such probes includes a set of four oligonucleotide probes which are identical in sequence save for one nucleotide position.

Each of the four probes includes a different nucleotide (A, G, C and T/U) at this position. The probes may be labeled with labels capable of producing different detectable signals that are distinguishable from one another, such as different fluorophores capable of emitting light at different, spectrally-resolvable wavelengths (for example, 4 differently colored fluorophores).

The primer pairs used in this invention can be obtained by chemical synthesis, recombinant cloning, or a combination thereof. Methods of chemical polynucleotide synthesis are well known in the art and need not be described in detail herein. One of skill in the art can use the target sequence to obtain a desired primer pairs by employing a DNA synthesizer or ordering from a commercial service.

Nucleic acid amplification requires a target nucleic acid in a buffer compatible with the enzymes used to amplify the target. The target nucleic acid used for this invention encompasses any reaction samples suspected to contain the target sequence. It is not intended to be limited as regards to the source of the reaction sample or the manner in which it is made. Generally, the test sample can be biological and/or environmental samples. Biological samples may be derived from human, other animals, or plants, body fluid, solid tissue samples, tissue cultures or cells derived therefrom and the progeny thereof, sections or smears prepared from any of these sources, or any other samples suspected to contain the target nucleic acids. Preferred biological samples are body fluids including but not limited to blood, urine, spinal fluid, cerebrospinal fluid, sinovial fluid, ammoniac fluid, semen, and saliva. Other types of biological sample may include food products and ingredients such as vegetables, dairy items, meat, meat by-products, and waste. Environmental samples are derived from environmental material including but not limited to soil, water, sewage, cosmetic, agricultural and industrial samples.

Preparation of nucleic acids contained in the test sample can be carried out according to standard methods in the art or procedures described. Briefly, DNA and RNA can be isolated using various lytic enzymes or chemical solutions according to the procedures set forth in Sambrook et al. ("Molecular Cloning: A Laboratory Manual"), or extracted by nucleic acid binding resins following the accompanying instructions provided by manufacturers' instructions.

The nucleic acid in the reaction sample can be cDNA, genomic DNA or viral DNA. However, the present invention can also be practiced with other nucleic acids, such as mRNA, ribosomal RNA, viral RNA. These nucleic acids may exist in a variety of topologies. For example, the nucleic acids may be single stranded, double-stranded, circular, linear or in form of concatamers. Those of skill in the art will recognize that whatever the nature of the nucleic acid, it can be amplified merely by making appropriate and well recognized modifications to the method being used.

In an aspect of the invention, a chip for running a reaction comprises an array of addressable units each being configured to run a chemical reaction. The addressable units of the chip are arranged according to a predetermined set of temperatures for running the chemical reactions of the units. At least one of the units is addressed to indicate the predetermined temperature for running the chemical reactions within the unit.

In an embodiment, a plurality of the units are addressed to indicate the predetermined temperature for running the chemical reactions. In another embodiment, each of the units is individually addressed to indicate the predetermined temperature for running the chemical reaction within said unit.

The predetermined temperature of a unit of a chip of the invention can be configured to yield at least 90% of homogeneous product from the chemical reaction. If the annealing temperatures are optimized, the configuration of an addressable chip based upon predetermined reaction temperatures can significantly improve the yield and quality of a reaction product. This can be important when a user is interested in analyzing a large number of nucleic acids, such as the whole genome of an organism, with a chip and the apparatuses of the present invention. In an embodiment, the improved reaction yield plays an important role in the use of a chip, apparatus, or system of the invention when used as a medical diagnostic instrument.

Figure 5:
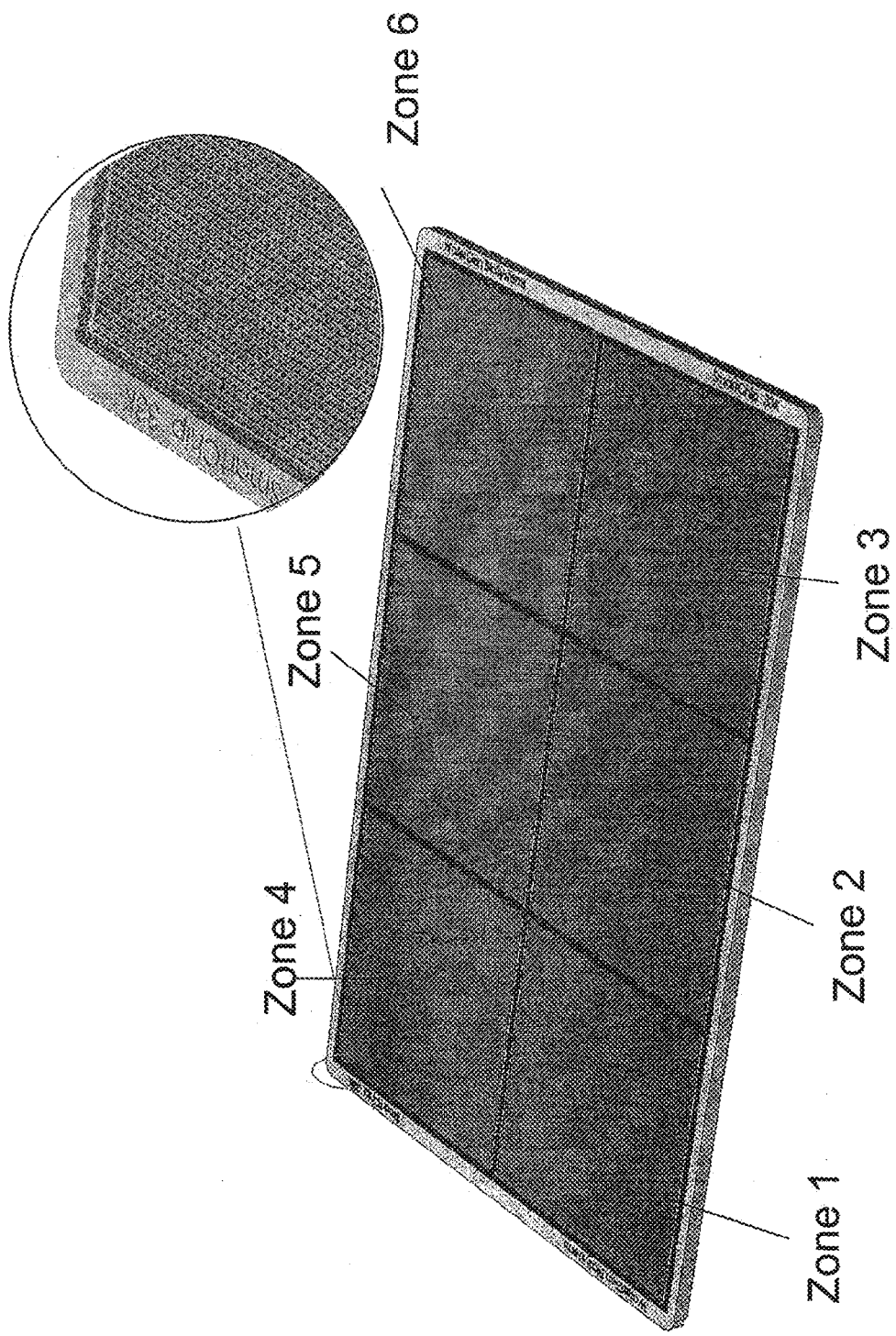
FIG. 5 illustrates an exemplary chip of the invention comprising a set of smaller chips that each represents a different temperature zone.

FIG. 5 illustrates an example chip 500 of the invention comprising a set of smaller chips 510. The set of smaller chips 510, also referred to as a plate 500, are placed in contact with a thermally insulative frame 530. Each smaller chip 510 represents a different temperature zone, as labeled in FIG. 5, in this example, zones 1, 2, 3, 4, 5, and 6. In an embodiment, the temperature zones correspond to a predetermined set of annealing temperatures for conducting polymerase chain reaction within the nanowells 520 of the chip 500. By separating the overall chip 500 into different temperature zones, a user can increase the specificity of the reaction within the nanowells 520. For example, when analyzing an entire genome of a species, a plurality of temperature zones can allow for more accurate determination of the genome.

The subject chips can contain one or more grooves etched in at the bottom side of the chip. In general, the grooves are under-trenches, open channels or paths to allow air passage. The grooves reduce the thermal mass of the chip, increase the surface area, and thus enhance the thermal performance of the chips. The grooves can be fabricated in any shapes, including but not limited to circular, elliptical, oval, conical, rectangular, triangular, and polyhedral. The grooves may be further divided by linear or curved walls to form separate but adjacent channels, or by circular walls to form inner and outer annular channels. The dimensions of the grooves will depend on the overall sizes and depths of the chips. The depths of the grooves may range from about one tenth to about nine tenths of the chip depths. The other dimensions, namely widths and lengths, may be shorter, longer or comparable to the corresponding dimensions of the chips. In particular, the L-shaped grooves surround the base of a unit. As the air flows through the passageways formed by any of the grooves, it removes heat from the surfaces of unit by passive heat dissipation, thus increasing the speed of thermal cycling.

Several factors apply to the selection of a suitable chip substrate. The substrate is often a good thermal conductor. A good thermal conductor generally has a thermal conductivity value higher than 1 $W/m^{-1}K^{-1}$, preferably higher than 100 $W/m^{-1}K^{-1}$, more preferably higher than 140 $W/m^{-1}K^{-1}$. Whereas the material's thermal conductivity may be 250 $W/m^{-1}K^{-1}$ or higher, it usually does not exceed 500 $W/m^{-1}K^{-1}$. Second, the substrate must be relatively inert and chemically stable. Such substrate generally exhibits a low level of propensity to react with the reaction samples employed in the intended application. Moreover, the materials should also be selected based upon the ability or feasibility to integrate the thermal control elements onto or adjacent to them. A variety of materials meet these criteria. Exemplary materials include but are not limited to metalloids or semiconductors, such as silicon, silicates, silicon nitride, silicon dioxide, gallium phosphide, gallium arsenide, or any combinations thereof. Other possible materials are glass, ceramics (including crystalline and non-crystalline silicate, and non-silicate-based ceramics), metals or alloys, composite polymers that contain dopants (for example, aluminum oxide to increase thermal conductivity), or any of a range of plastics and organic polymeric materials available in the art. In one embodiment, the nanowells are fabricated in such substrates including Al or SS-316 as well as similar others.

In an embodiment, the chips are fabricated using a thermally conductive polymer. For example, the chips can be fabricated using polycarbonate, polypropylene, or any other conductive polymer known to those with skill in the art.

The chips can be fabricated by any method as would be obvious to one skilled in the art. Examples of method of making a chip of the invention include, but are not limited to, micro drilling, electric discharge method, hot embossing, and hot embossing with a tool made from which uses water as light guide.

Alternatively, chips of the present invention can be fabricated using techniques well established in the Integrated Circuit (IC) and Micro-Electro-Mechanical System (MEMS) industries. The fabrication process typically proceeds with selecting a chip substrate, followed by using appropriate IC processing methods and/or MEMS micromachining techniques to construct and integrate various components.

Fabrication of the subject chips can be performed according to standard techniques of IC-processing and/or MEMS micromachining. The subject chips can be fabricated as multi-layer structures. The process generally proceeds with constructing the bottom layer. Then a combination of techniques including but not limited to photolithography, chemical vapor or physical vapor deposition, dry or wet etching are employed to build structures located above or embedded therein. Vapor deposition, for example, enables fabrication of an extremely thin and uniform coating onto other materials, whereas etching allows for mass production of larger chip structures. Other useful techniques such as ion implantation, plasma ashing, bonding, and electroplating can also be employed to improve the surface properties of the chips or to integrate various components of the chips. The following details the fabrication process with reference to the exemplary chip designs depicted in the figures. The same general process and the apparent variations thereof are applicable to fabricate any of the subject chips described herein.

FIG. 4 is a cross-section view of a portion of an exemplary chip design. In this embodiment, the nanowell is embedded within a body which is made up of first and second (or bottom and top) layers of substrates respectively. The process begins with providing a first layer of substrate which is generally a heat resistant material such as glass, Pyrex wafer, or any other suitable materials described herein or known in the art. The next step is to create the nanowell that forms the basis of the unit. The nanowell is generally disposed within the second layer that is typically a silicon wafer (see, for example, FIG. 4). The silicon wafer may go through several processing steps prior to being attached to the first layer. For example, the silicon wafer may be attached to a layer of photoresist to render the surface more susceptible to chemical etching after exposure to UV light during the process of photolithography. The layer of photoresist defines, by precise alignment of the photo-mask, the size and location of the nanowell that is to be formed by a subsequent etching step. The silicon wafer is then etched by a variety of means known in the art to form the well cavity. A commonly practiced etching technique involves the use of chemicals, for example, potassium hydroxide (KOH), which removes the silicon wafer to form the desired shape.

Once the nanowells of the subject chips are fabricated, their surface properties can be improved to suit the particular application. Where large surface area is desired, the wall of the nanowell may be further etched by, for example, a plasma etcher to obtain very fine dendrites of silicon, commonly referred to as "black silicon". The presence of black silicon can dramatically increase the effective heating surface area. The black silicon fabricated at the base of the nanowell may also serve as an anchor for photon-sensing devices, temperature sensors and other control elements.

As discussed herein, a nanowell of high inner surface to volume ratio may be coated with materials to reduce the possibility that the reactants contained therein may interact with the inner surfaces of the well. The choice of methods for applying the coating materials will depend on the type of coating materials that is used. In general, coating is carried out by directly applying the materials to the nanowell followed by washing the excessive unbound coating material. Certain coating materials can be cross-linked to the surface via extensive heating, radiation, and by chemical reactions. Those skilled in the art will know of other suitable means for coating a nanowell fabricated on chip, or will be able to ascertain such, without undue experimentation.

Sample preparation then includes combining the PCR reaction sample mixture, the labeled primers, and the sample with a drop of oil which can be individually nano dispensed to prevent evaporation. The sample is then dispensed into the individual nanowells using a piezo dispenser and a dew point dispensing technique.

To prevent evaporation of aqueous reaction samples, the samples can be applied to the nanowell at or around dew point. As used herein, "dew point" refers to a temperature range where the droplet size does not change significantly. At dew point, an equilibrium is reached between the rate of evaporation of water from the sample droplet and the rate of condensation of water onto the droplet from the moist air overlying the chip. When this equilibrium is realized, the air is said to be saturated with respect to the planar surface of the chip. At one atmospheric pressure, the dew point is about 14° C. Accordingly, dispensing aqueous reaction samples is preferably carried out at a temperature no more than about 1° C. to about 5° C. degrees above dew point. As is apparent to one skilled in the art, dew point temperature increases as the external pressure increases. Therefore, where desired, one may dispense the reaction samples in a pressured environment to prevent evaporation.

Amplified nucleic acids present in the subject chips may be detected by a range of methods including but not limited to (a) forming a detectable complex by, for example, binding the amplified product with a detectable label; and (b) electrophoretically resolving the amplified product from reactants and other components of the amplification reaction.

In certain embodiments, the amplified products are directly visualized with detectable label such as a fluorescent DNA-binding dye. Because the amount of the dye intercalated into the double-stranded DNA molecules is typically proportional to the amount of the amplified DNA products, one can conveniently determine the amount of the amplified products by quantifying the fluorescence of the intercalated dye using the optical systems of the present invention or other suitable instrument in the art. DNA-binding dye suitable for this application include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, and the like.

In addition to various kinds of fluorescent DNA-binding dye, other luminescent labels such as sequence specific probes can be employed in the amplification reaction to facilitate the detection and quantification of the amplified product. Probe based quantitative amplification relies on the sequence-specific detection of a desired amplified product. Unlike the dye-based quantitative methods, it utilizes a luminescent, target-specific probe (for example, TaqMan® probes) resulting in increased specificity and sensitivity. Methods for performing probe-based quantitative amplification are well established in the art and are taught in U.S. Pat. No. 5,210,015.

In various embodiments, the chip additionally comprises alignment features, operable to align or attach a cover to the chip or to align or attach the chip to a heating element. In various embodiments, such features comprise concave or convex features. Such features include pins, ridges, snaps, screws, and combinations thereof.

In various embodiments, the chip assembly comprises a temperature control element, which facilitates the monitoring or control of the temperature of reaction chambers. Such temperature control elements include but are not limited to channels or other structures that facilitate the flow of a heating or cooling gas through the assembly.

In another aspect of the invention, a method of conducting a reaction that involves a plurality of reaction samples and requires cycling at least two temperature levels is disclosed and comprises: providing a chip comprising an array of addressable units each being configured to run a chemical reaction, wherein the units are arranged according to a predetermined set of temperatures for running the chemical reactions of the units, such that at least one of the units is addressed to indicate the predetermined temperature for running the chemical reactions within said unit; placing the plurality of reaction samples into the units of the chip according to the set of predetermined temperatures; and controlling a heating element to effect cycling at least two temperature levels. In one aspect a method of conducting a chemical reaction can include providing a chip as described herein where the chip is configured to receive a reaction sample. A heating element can be provided that is positionable in relation to the chip to provide thermal contact between at least one heating element and the chip. A chemical reaction can be conducted in the reaction sample by varying the temperature of the chip. Varying the temperature in the chip can be effected, for example, by moving at least one heating element in relation to the chip such that the heating element is in thermal contact with the chip.

The method uses a chip of the invention and a thermal cycling apparatus or the invention. Typically, in the analysis of an entire genome of an organism, amplification of different genes or nucleic acid sequences are optimized at different annealing temperatures. These different annealing temperatures could be grouped into general zones to improve the sensitivity and specificity of an assay. A chip of the invention can therefore be addressed according to one of the annealing temperature zones.

The selection of the annealing temperature can be a critical component for optimizing the specificity of a PCR reaction. The annealing temperatures of different sequences for nucleic acid amplification can be determined in a variety of ways. One method is to determine the melting temperature ($T_m$) of a nucleic acid sequence. The melting temperature is the temperature at which one half of the DNA duplex will dissociate and become single stranded. When designing a nucleic acid amplification, primer length and sequence are important in designing the parameters of a successful amplification. For example, the melting temperature of a DNA increases both with its length, and with increasing guanine and cytosine content which can be approximated using a simple formula.

The annealing temperature chosen for a PCR reaction depends directly on length and composition of the primer(s). The annealing temperature ($T_a$) can be chosen to be about 5° C. below the lowest $T_m$ of the pair of primers to be used (Innis and Gelfand, 1990). Another example method of calculating the annealing temperatures is:

$$T_a Opt = 0.3 \times (T_m \text{ of primer}) + 0.7 \times (T_m \text{ of product}) - 25$$

where $T_m$ of primer is the melting temperature of the less stable primer-template pair and $T_m$ of product is the melting temperature of the PCR product (Rychlik, et al., 1990).

If the annealing temperature of a PCR reaction is too low, a primer can anneal to sequences other than the true target, and can lead to non-specific amplification and consequent reduction in yield of the desired product. A consequence of too high an annealing temperature is that too little product will be made, as the likelihood of primer annealing is reduced. Another consideration is that a pair of primers with very different annealing temperatures may never give appreciable yields of a unique product, and may also result in inadvertent asymmetric or single-strand amplification of the most efficiently primed product strand.

In PCR thermal cycling, the optimum $T_a$ and the maximum $T_a$ range for each different primer pair and can vary from gene to gene in a continuous fashion. Typically, the anneal temperature to produce high quality anneal for a given primer pair is in a range of 1 to 3° C. If the anneal temperature is higher, the PCR anneal step can slow down; if it is lower, the primers might bind to the DNA at sites other than the desired ones or to other species.

One method is to "bin" the gene assays; the temperature of a given assay is assigned to the addressable portion of the chip with the temperature closest to that of $T_a$ of that given gene assay. For example, if the apparatus or chip has 3 temperature zones of 60, 62.5 and 65° C., an assay that has an optimum behavior $T_a$=64° C. is assigned to the 65° C. zone.

The annealing step of a PCR reaction typically occurs in 40 sec or less, depending partially on the length of the sequence to be amplified.

While the PCR is normally started at 5° C. below the calculated temperature of the primer melting point ($T_m$), the optimum temperature often can be much higher than the calculated temperature. In some embodiments, the annealing temperature must be empirically tested. For example, multiple PCR reactions with gradually increasing temperatures can be carried out until the optimal annealing temperature is determined.

Many of the genetic sequences in a genome can be grouped into temperature zones. In an embodiment, the units of a chip of the invention represent different annealing temperature zones, for example, the zones are 2° C. increments over the range of 54 to 68° C. The units are then addressed according to predetermined temperature at which the annealing step of the PCR reaction will occur.

After a unit is addressed according to a predetermined temperature, sample can then be dispersed into the chip. The sample can be added to the chip by a variety of methods as disclosed herein.

In various embodiments, a system or chip can additionally comprise a filling device, which is operable to facilitate filling of amplification reagents or samples into the addressable units of the chip. Filling devices among those useful herein include physical and chemical modalities that direct, channel, route or otherwise effect filling reagents or samples into the addressable units.

In various embodiments, the chip may comprise raised or depressed regions, for example, features such as barriers and trenches to aid in the distribution and flow of liquids on the surface of the chip. In an embodiment, the filling system comprises capillary channels. The dimensions of these features are flexible, depending on factors, such as avoidance of air bubbles upon assembly and mechanical convenience and feasibility.

The filling system comprises any apparatus which facilitates the placement of amplification reagents or sample on the surface of the chip, preferably effecting placement of such reagents or sample in addressable units. Such apparatus among those useful herein include devices for pouring of reagents or samples onto the surface so as to substantially cover the entire surface. In an embodiment the filling system comprises a device for pipetting, spotting or spraying of reactants to specific reaction chambers (for example, by use piezoelectric pumps). The filling system can be a nano-dispenser. In another embodiment, the filling apparatus comprises a vacuum pump operable to fill the reaction chambers of the chip. Filling systems may also include devices for applying centrifugal force to the chip. In one embodiment, the filling system is in close proximity to or in fluid communication with d filling device in the chip. The filling system can operate automatically or according a protocol from a computer.

Apparatus

One aspect of the present invention is the design of an apparatus configured to receive a miniaturized chip designed for the multiplexed analyses of individual molecules, and/or simultaneous performance of a vast number of chemical reactions. In one embodiment, the present invention provides a highly automated, miniaturized; analytical instrument that allows manipulations with precise control of temperature, evaporation, small-volume reagent delivery, and/or product detection in a multiplexed fashion.

The apparatus of one aspect of the invention includes at least one heating element useful for heating or cooling a chip. It is to be understood that where the heating element is configured to reduce the temperature of a chip, the component functions essentially as a cooling element.

In one embodiment the apparatus includes a base with at least one heating element positioned on the base. The heating element can provide a range of useful temperatures. For example, the heating element can be configured to provide a temperature in the range between about −20° C. to about 120° C. as desired.

The heating element can be configured to receive a chip. In various embodiments the heating element can be positioned either below the chip or above the chip. In a particular embodiment where only one heating element is present, the heating element can move relative to the chip. Where desired, the chip can be stationary.

Figure 6:
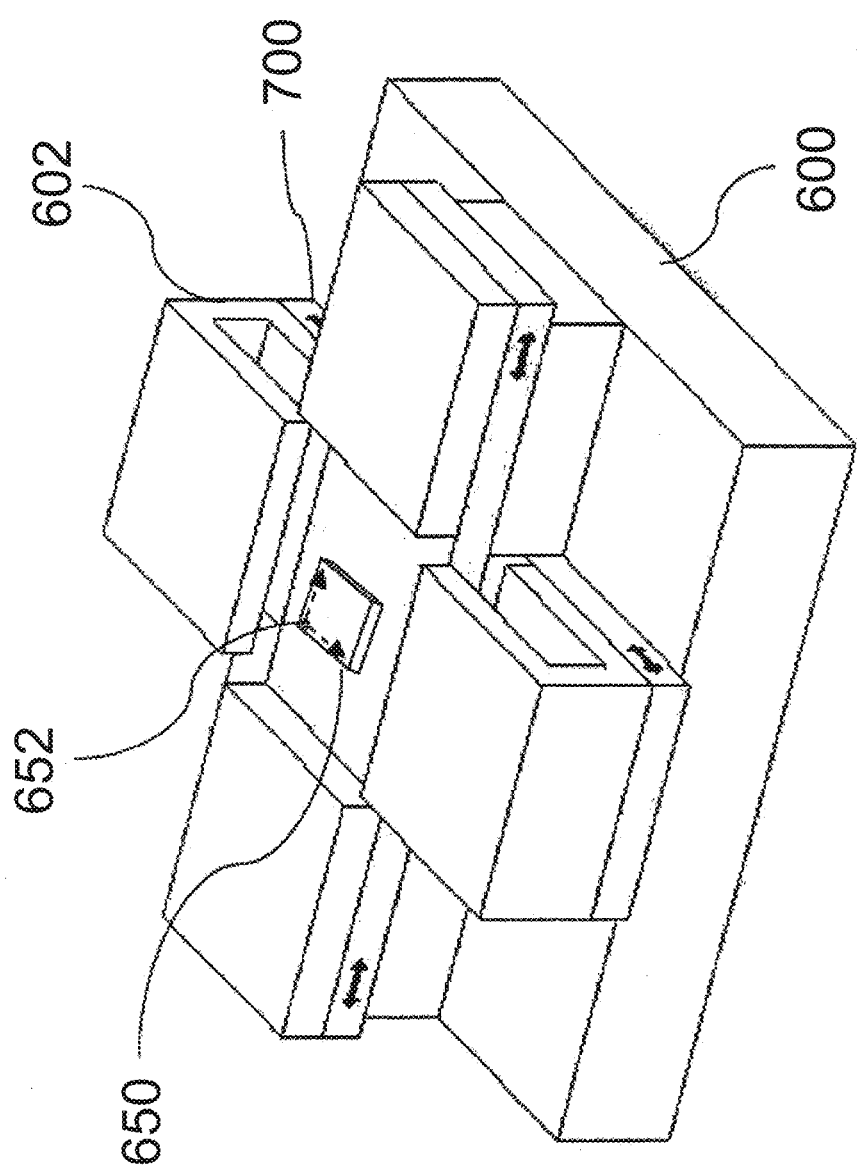
FIG. 6 depicts one illustrative apparatus design having at least one heating element with a nanowell chip.

FIG. 6 is a non-limiting example of a schematic diagram of the one embodiment of the apparatus. FIG. 6 depicts a base 600 with at least one heating element 602 positioned on the base 600. The heating element 602 is adapted to receiving a chip 650, such chip is capable of containing and confining a reaction sample in one of the nanowells 652 on the chip 650. The heating element 602 of the apparatus can be moved in two positions relative to the chip 650.

Figure 7:
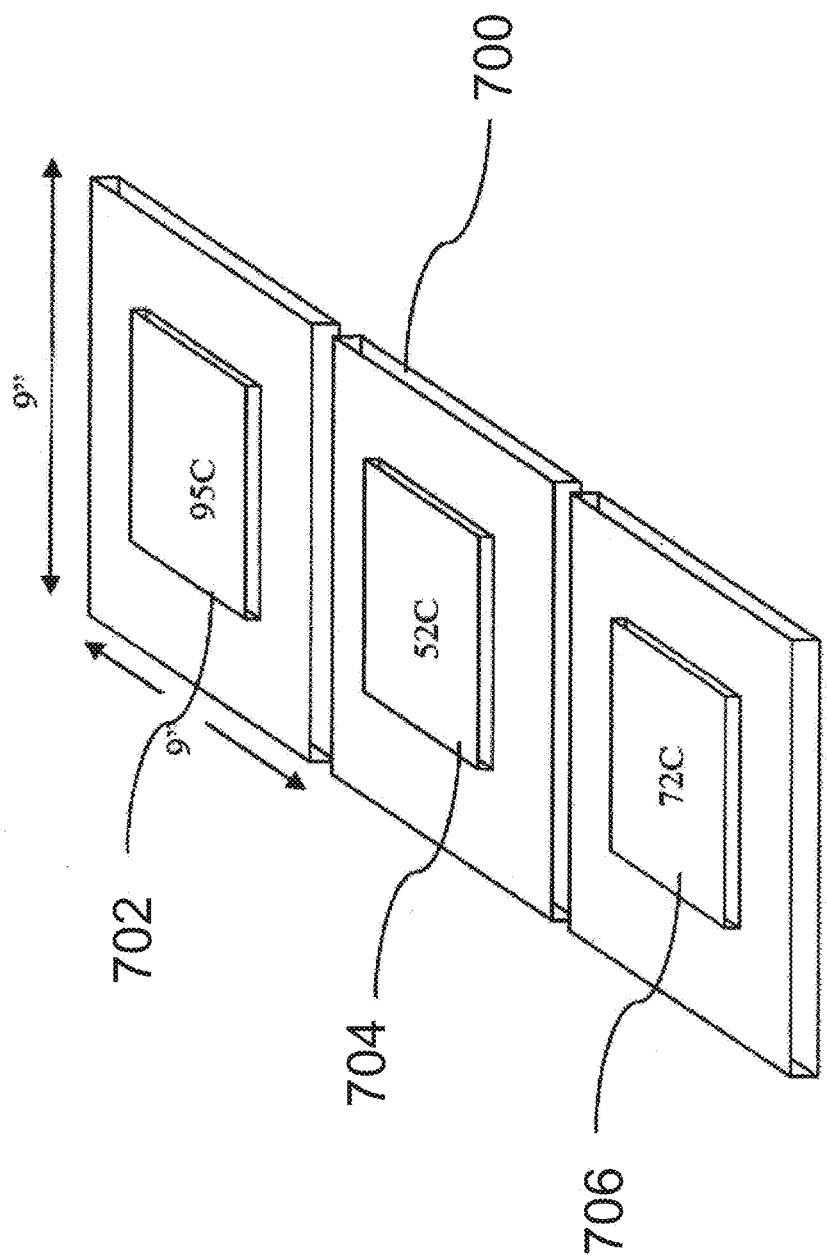
FIG. 7 is an illustrative drawing of an apparatus of one embodiment of the invention with more than one temperature zone.

The heating element 602 as seen in FIG. 6 can be divided into different temperature zones as seen in FIG. 7. FIG. 7 is an illustrative drawing of a heating element positioned below the chip 700 used to control and/or vary the temperature of a chip. In one embodiment the temperature ranges for a heating element can be in the range of 90° C. to 95° C. for the denaturation temperature, 52° C. to 65° C. for the primer annealing stage, and 68° C. to 75° C. for the primer-dependent extension stage. A non-limiting example of a heating element 700 is shown in FIG. 7. The heating element 700 in this example is one with temperature zones of 95° C. (702), 52° C. (704), and 72° C. (706) for the denaturation, primer annealing stage and primer-dependent extension stage of PCR, respectively. The dimensions of each temperature zone of the heating element 700 can vary in size. In one embodiment depicted in FIG. 7, the heating element positioned below an example of the chip is about 9 inches in length by 9 inches in width.

A chip adapted to containing and confining a reaction sample is then placed on the heating element 700 of the apparatus adapted to receiving the chip. Using the heating element positioned below 700 the chip of FIG. 7, the heating elements then physically moved so that the chip comes in contact with the 95° C.-block, followed by the 52° C.-block, and then the 72° C.-block. The movement of the heating element respective to the chip allows the critical ramp down rates to be a lot faster due to the larger surface area on the heating element. The larger surface area also allows for cooling from the backside of the chip due to transfer of the chip from temperature to temperature. This technique also allows the chip to be heated and cooled at a much faster rate than the traditional way of simply cooling the chip between cycles.

Figure 8:
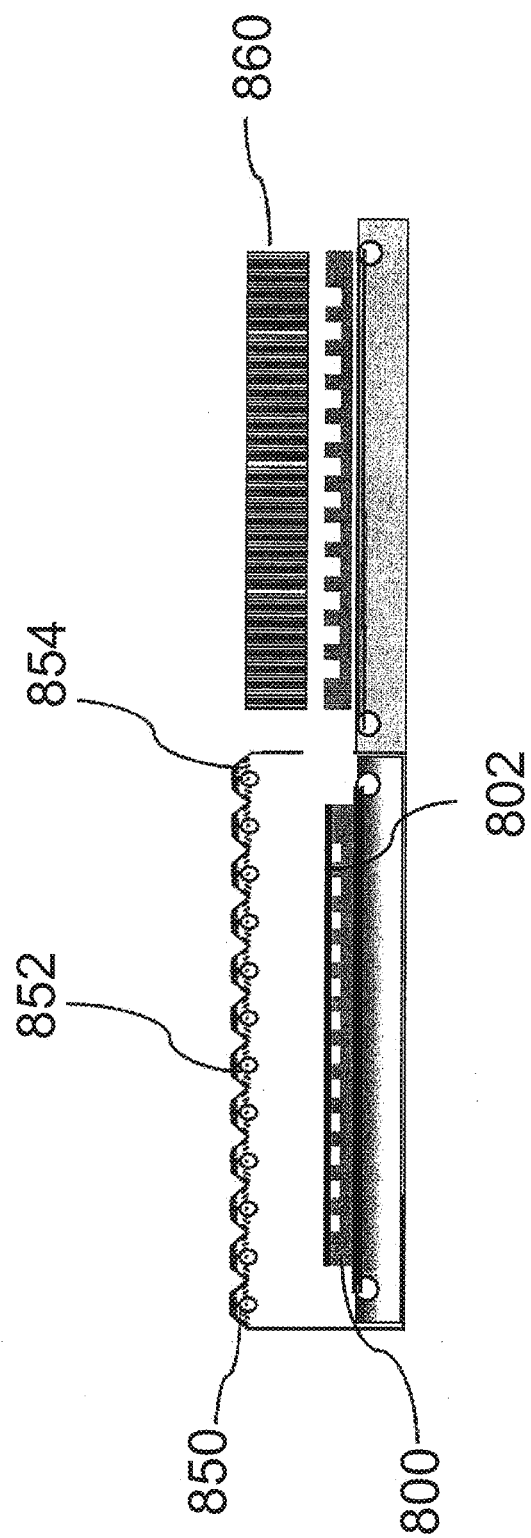
FIG. 8 is a side view of one embodiment of apparatus of one embodiment of the invention with a top mounted heating element and an optical scanner.

Another method for controlling and/or varying the temperature of the chip 800 is depicted in FIG. 8. FIG. 8 is a non-limiting example of the heating element 850 positioned above the chip 800. As shown in FIG. 8, the heating element can be a series of on/off arc halogen lamps 852 positioned above the chip 800. Heat reflectors 854 are positioned around each halogen lamp 852 to ensure a uniform heat source from the heat lamps 852. The high output power of the arc lamp 852 and the spectral match of the output to silicon provides a very fast "ramp up" rate of the arc lamps 852. The fact that the lamp is an arc lamp means that switch off of the arc lamp 852 is virtually instantaneous. FIG. 8 also shows that the chip 800 can also be sealed with a radiation curable adhesive 802 to help prevent evaporation of the reaction sample. Following a reaction cycle, in one non-limiting example the chip is then scanned with a scanner 860, for example, a hyper spectral or CCD Scanner. In certain aspects, such an optically coupled system transmits excitation beams into the wells containing the reaction samples at a plurality of times during the amplification, and monitors the optical signals coming from the nanowells at each of the plurality of times between cycles.

Figure 9:
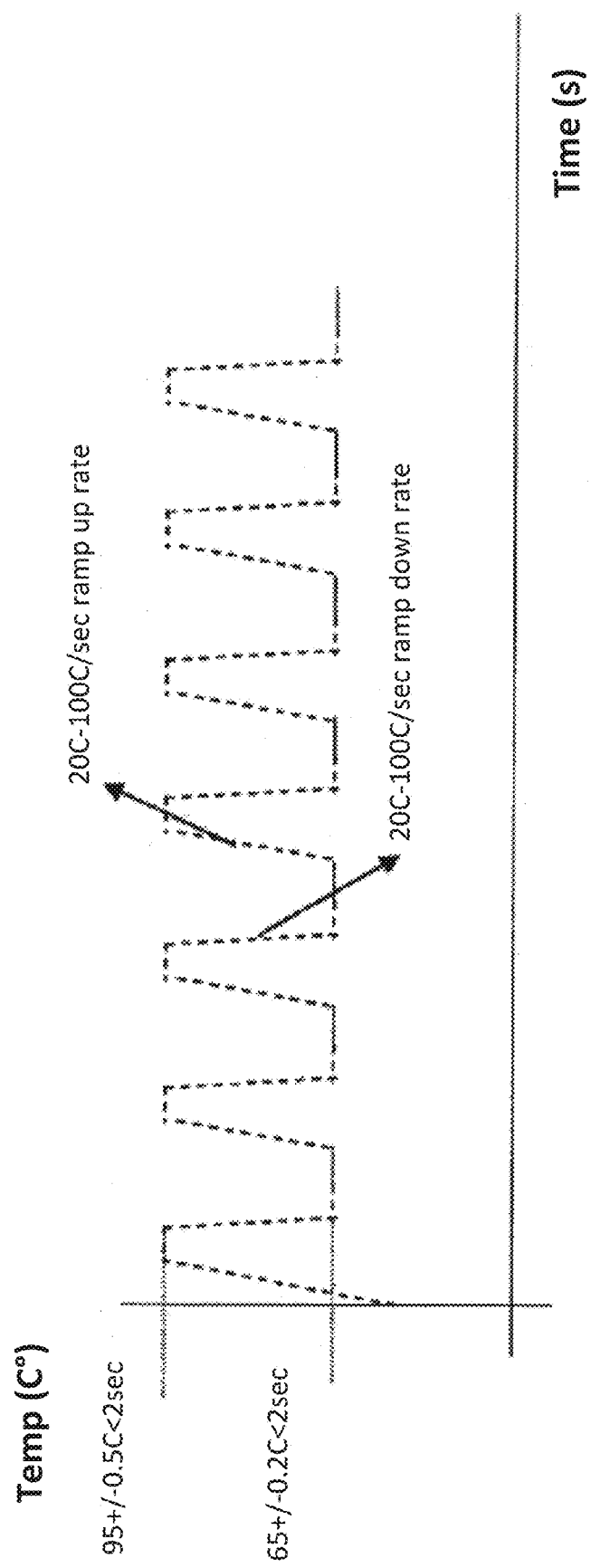
FIG. 9 is a graph plotting the changes in temperature of apparatus (y-axis) at various times (x-axis).

FIG. 9 graphically shows the change in temperature in Celsius (y-axis) versus time in seconds (x-axis) of the on/off arc lamps. As seen in FIG. 9, the halogen lamps ramp up rate of the arc lamp is 20° C. to 100° C./sec for a temperature of 95+/−0.5° C. in less than about 2 seconds and has a 20° C. to 100° C. ramp down rate to 65+/−0.5° C., also in less than about 2 seconds. The temperature of the arc lamp shifts from approximately 65° C. to approximately 95° C. during the PCR reaction process.

Where desired, the subject devices are designed to minimize the movement of pulsed heat into the nanowells fabricated out of Aluminum/Silicon in an alternative chip. One way to minimize the amount of pulsed heat is to reduce the time that the Al/Si spends at the highest temperatures and thereby reducing "thermal budget". Speeding the "ramp-up" and "cool-down" rates and providing the fastest possible transition from heating to cooling, or "turn around" is therefore important. This method of heating and cooling the chip also ensures uniformity in the heating of the chip. Such uniformity prevents stresses due to temperature differences of a few degrees that can lead to variations in the performance of the nanowells.

Figure 10:
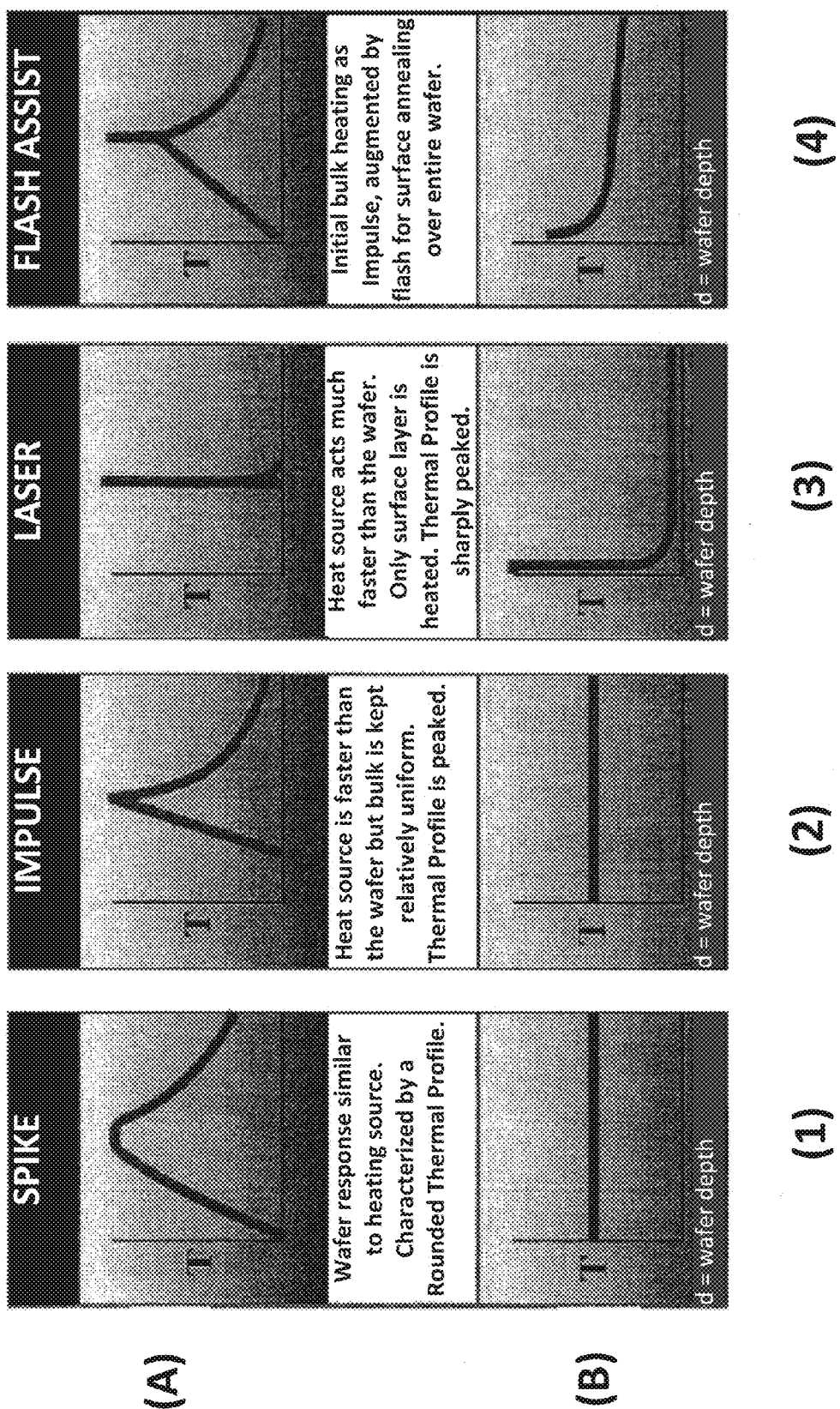
FIG. 10 depicts a series of thermal temperature profiles capable of being produced by the arc lamps. Each temperature profile shows the chip response to the heating element. The top row of graphs (a) shows the change in temperature (y-axis) over time (x-axis). The bottom row of graphs (b) show the temperature of the chip (y-axis) over the depth of the chip (x-axis).

As seen in FIG. 10, there are several temperature output profiles that the arc lamps are capable of delivering. The graphs along row (a) show the change in temperature (y-axis) versus the change in time (x-axis). Correspondingly, the graphs along row (b) depict the chip response to the rapid thermal processing (RTP) profiles depicted in row (a). In response to a slower change in temperature over time, such as in a spike or impulse optical heater profile, the chip temperature remains constant over the entire depth of the chip. In response to a more rapid change in temperature over time, such as in a laser or flash assist heater profile, the temperature of the chip varies depending on the depth of the chip relative to the heating source.

Without being limited to a particular theory, FIG. 10 illustrates a number of temperature output profiles corresponding to the invention. The spike heater profile, as seen in FIG. 10(*a*)(1), which is characterized by a rounded thermal profile, generates a chip response temperature similar to the heating source temperature, as seen in FIG.

10(b)(1). In the impulse heater profile (FIG. 10(a)(2)), characterized by a peaked thermal profile, the temperature of the heat source is faster than the temperature of the chip in response to the heat source, but the temperature of the chip is still kept relatively uniform over the entire depth of the chip relative to the distance from the heat source (FIG. 10(b)(2)). For a laser heater profile as seen in FIG. 10(a)(3), characterized by a sharply peaked profile, the heat source acts much faster than the chip. Therefore, only the surface layer of the chip is heated (FIG. 10(b)(3)). The deeper the depth of the chip, the cooler the temperature profile. Finally, for the flash assist profile (FIG. 10(a)(4)), characterized by initial bulk heating followed by a flash for surface annealing, the chip response is similar to the chip response to the laser profile (FIG. 10(b)(4)).

In another aspect of the invention, an apparatus is described for conducting a chemical reaction requiring cycling at least two temperature levels, that comprises: a chip for running a reaction comprising an array of addressable units each being configured to run a chemical reaction, wherein the units are arranged according to a predetermined set of temperatures for running the chemical reactions of the units, such that at least one of the units is addressed to indicate the predetermined temperature for running the chemical reactions within said unit; and a heating element in thermal contact with the chip.

In a preferable embodiment, the addressable units of the chip are configured to run a nucleic acid amplification reaction, including but not limited to real-time PCR. The units can be nanowells that comprise a reagent, a probe, a primer, a dNTP, or a combination thereof. The predetermined temperatures can be different annealing temperatures for carrying out a PCR reaction.

The heating element can be a simple heater, such as a plate comprising a resistive heater or a thermoelectric heater, or an elaborate thermal cycling apparatus. In some examples, the heating element is thermal contact with a heat sink to allow for rapid temperature changes of the chip when the chip is in thermal contact with the heating element. A fan could also be coupled to the heating element to provide more control over rapid thermal cycling. Other examples of heating elements include thin film heaters that can be heated rapidly by conduction or have electromagnetic heaters incorporated into the film. A material particularly suitable for fabricating the thin film heaters is indium tin oxide (ITO). ITO is a transparent ceramic material with a very high electrical conductivity. Because ITO can be prepared in bulk or in form of thin layer, it is particularly useful as either an integral or an external heating element.

In another embodiment, heating elements are compatible to the chips in terms of size and configuration. In an embodiment, the apparatus further comprises a plurality of heating elements. The heating element can be placed as a detachable unit adjacent to, at the base and/or on top of the chip. In a preferable embodiment, the heating element area is significantly larger than the chip area, in order to minimize edge effects at the edges of a heating element.

Figure 11:
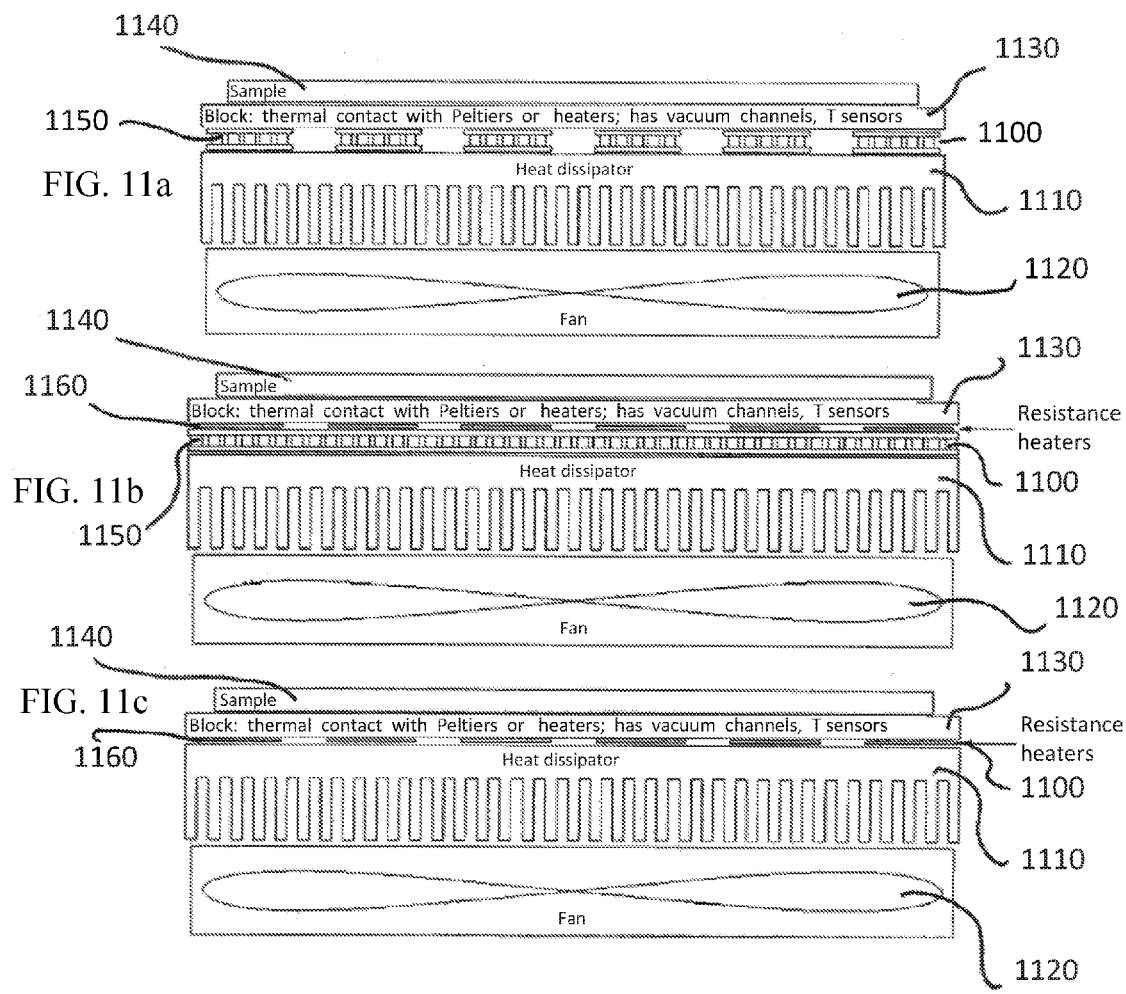
FIGS. 11a-c represent examples of different heating element configurations of a thermal cycling apparatus.

Some examples of heating element construction and setup are illustrated in FIGS. 11a-c. In these examples, the heating elements 1100 are coupled to a heat sink 1110 and a fan 1120 to improve control over temperature changing and ramp up times for thermal cycling. A metal thermal block 1130 can be used between the heating element 1100 and the sample (or chip) 1140 that is in intimate thermal contact with the element 1100 and the chip 1140. The block 1130 can have a high thermal conductivity even if the chip 1140 might not have a high thermal conductivity, to produce a reproducible temperature change. If multiple heating elements are used to define a temperature zone or multiple temperature zones, any small disturbance of the heating (for example, an air breeze) can produce a significant change in temperature. If the resistance is made low using a thermal block, the transfer of heat from zone to zone can be smoothed. In addition, the metal thermal block can hold temperature sensors on the top surface. The temperature sensor can correspond to each zone, or can be part of the chip itself. The thermal block can also provide vacuum channels to allow vacuum to hold the chip in intimate thermal contact with the block and/or heating elements. As demonstrated in FIGS. 11a-c, the heating element 1100 can comprise one or a plurality of thermoelectric 1150 or resistive 1160 heating elements, or a combination of both.

The heating element can provide a temperature gradient. The temperature gradient herein can be a temperature that is higher in a portion than another portion across a single heating element. For example, a resistive or thermoelectric heater can be configured to create a thermal gradient across the heating element. The thermal gradient can also be defined as a temperature that is higher in one portion than another portion of the chip. For example, if a plurality of heating elements are used, one heating element could deliver a higher temperature to one side or end of the chip and a second heating element could deliver a different temperature to one side or end of the chip, thereby creating a thermal gradient.

The apparatus can further comprise an optical system operatively coupled to the chip, wherein the optical system detects an optical signal coming from a unit. In one exemplary embodiment, the chip, heating element, and optical system make up a system of the invention.

In an aspect, the invention disclosure includes an apparatus for conducting a chemical reaction involving cycling at least two temperature levels comprising: a body configured to receive a sample holder for containing the chemical reaction; a first heater comprising a plurality of temperature zones; and a second heater providing a uniform temperature, wherein the first heater and the second heater are configured to be movable between a first and a second orientation, and wherein the first orientation places the heater in thermal contact with the sample holder and the second orientation does not place the heater in thermal contact with the sample holder.

The sample holder can be a chip for running a reaction comprising an array of addressable units each being configured to run a chemical reaction, wherein the units are arranged according to a predetermined set of temperatures for running the chemical reactions of the units, such that at least one of the units is addressed to indicate the predetermined temperature for running the chemical reactions within said unit. In an embodiment, the plurality of temperature zones correspond to the predetermined set of temperatures according to which the units are arranged.

In an embodiment where the apparatus and sample holder are configured to conduct a PCR reaction, the predetermined temperature zones correspond to different annealing temperatures at which multiple PCR reactions can be run. In a further embodiment, the apparatus and sample holder are capable of conducting a series of PCR reactions in order to amplify most, if not all, of a genome. In this example, an entire genome requires a range of annealing temperatures to achieve the desired specificity of a reaction. For example, these temperatures can be grouped into 2° C. temperature zones according to the annealing temperatures of different nucleotide, sequences. The units of a sample holder can be addressed according to the temperature zone at which the reaction within the unit is to be run. In an embodiment, the apparatus receives a sample holder that comprises a chip with units addressed according to six different annealing temperature zones corresponding to six different temperature zones on the first heater of the apparatus.

In a preferable embodiment, the first and second heaters move between the first and second orientations according to a protocol. The apparatus can further comprise a motor for moving the first and second heaters between the first and second orientations. The heaters can be moved by any method as would be obvious to those skilled in the art.

The first orientation puts a heater in thermal contact with the sample holder. In an embodiment, the sample holder is used to conduct a PCR reaction. The first heater has a plurality temperature zones, and can be used to provide the temperatures necessary for the annealing steps of a PCR reaction when the first heater is brought into thermal contact with the sample holder. In an embodiment, the second heater provides a temperature necessary for elongation or denaturation of a nucleic acid during a PCR reaction when the second heater is in the first orientation and thermal contact with a sample holder.

In an example of the apparatus and method of the invention, the second heater is moved into the first orientation in thermal contact with the sample holder for a PCR reaction. The second heater delivers a temperature of around 95° C., in order to denature a nucleic acid in a sample contained within the sample holder. After the denaturation step, the second heater is moved into the second orientation and the first heater is moved into the first orientation in thermal contact with the sample holder. The first heater provides temperatures to the sample holder for the annealing of a primer to a nucleic acid sequence of the sample. The process of conducting a denaturation step followed by an annealing step can be repeated or cycled until the desired amplification product is achieved.

Figure 12:
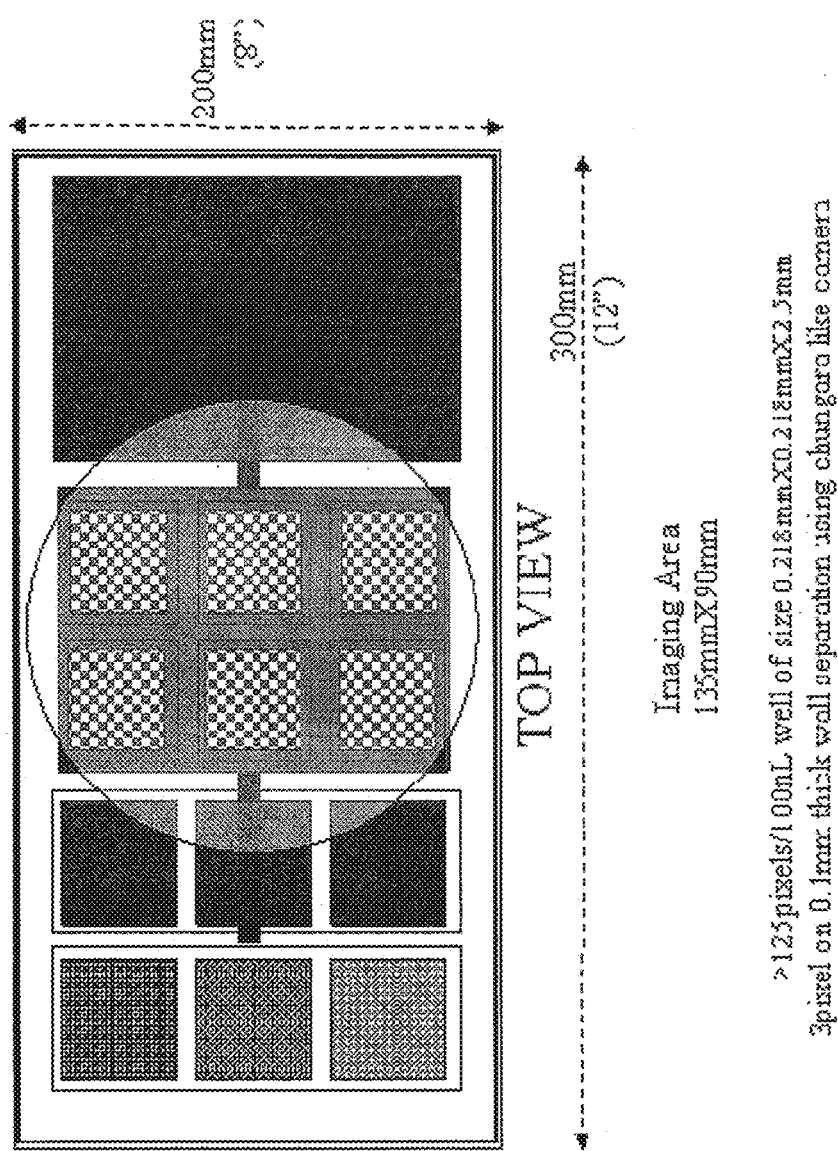
FIG. 12 demonstrates an exemplary embodiment of a thermal cycling apparatus wherein two heaters are movable between a first orientation and second orientation, wherein the first orientation is in thermal contact with a sample holder.

FIG. 12 demonstrates an example embodiment of a thermal cycling apparatus 1200 of the invention. In this example, the apparatus 1200 comprises a first heater 1210 with 6 different temperature zones corresponding to 6 different addressable predetermined temperatures of a chip 1250. The first heater 1210 can be moved in and out of thermal contact with the chip 1250 as shown in the top view in FIG. 12. The second heater 1220 provides a uniform temperature across the entire heater in order to heat each of the 6 different addressable predetermined temperature areas of the chip 1250 to the same temperature. For example, the second heater 1220 can provide uniform temperatures for the denaturation and elongation steps of conducting PCR with a chip of the invention, while the first heater 1210 can provide a range of annealing temperatures to increase the specificity of conducting a large number of reactions. An imaging source 1260 for analyzing the many reactions can be positioned on the opposite side of the chip from the first orientation of the heaters.

Figure 13:
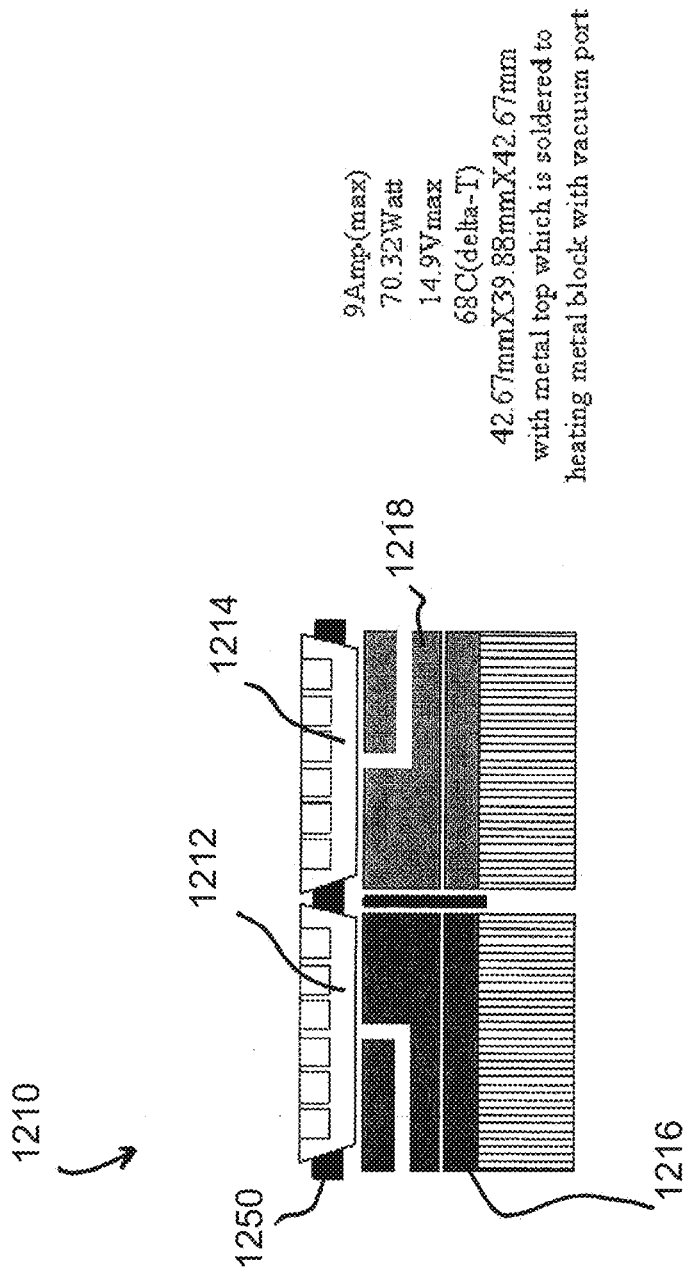
FIG. 13 demonstrates a side view of the first heater from the example in FIG. 12 when the heater is in the first orientation in thermal contact with a chip with addressable units.

FIG. 13 demonstrates a side view of the first heater 1210 from the example in FIG. 12 when the heater 1210 is in the first orientation in thermal contact with a chip with addressable units 1250. For example, each temperature zone 1212, 1214 of the heater can be provided by a different thermoelectric heating element 1216, 1218 and some example specifications are shown in FIG. 13.

In an embodiment, the first heater can provide a temperature gradient. Examples of types of heaters for the first and second heaters include, but are not limited to, a resistive heater and a thermoelectric heater.

In a further embodiment, the apparatus comprises a heat sink in thermal contact with the first heater, the second heater, or both.

In order to monitor temperature, the apparatus can also comprise a plurality of temperature sensors. In an embodiment, the plurality of temperature sensors have at least one temperature sensor assigned to measure the temperature of each temperature zone of the apparatus. The temperature sensor can be a thermocouple or any other sensor that are available in the art.

The heating element can be connected via electric leads to a power source that provides voltage across the element and effects subsequent heating of the units. The heating element may also be coupled to a temperature sensor that monitors and regulates the temperature of the unit. The temperature sensor may control the temperature and hence the thermal profile of an array of units. Dividing the chip and/or first heater into various temperature zones provides additional flexibility for parallel performance of chemical reactions that require different thermal cycling profiles. Alternatively, the temperature sensor can be coupled to individual unit or zone so that the temperature of each unit or zone can be independently controlled. The temperature sensor may be included as a detachable unit located adjacent to or at the base of the unit. It can also be integrated into the interior or the exterior surface of the unit. Furthermore, the temperature sensor can be fabricated as an integral part of the heating element.

Figure 14:
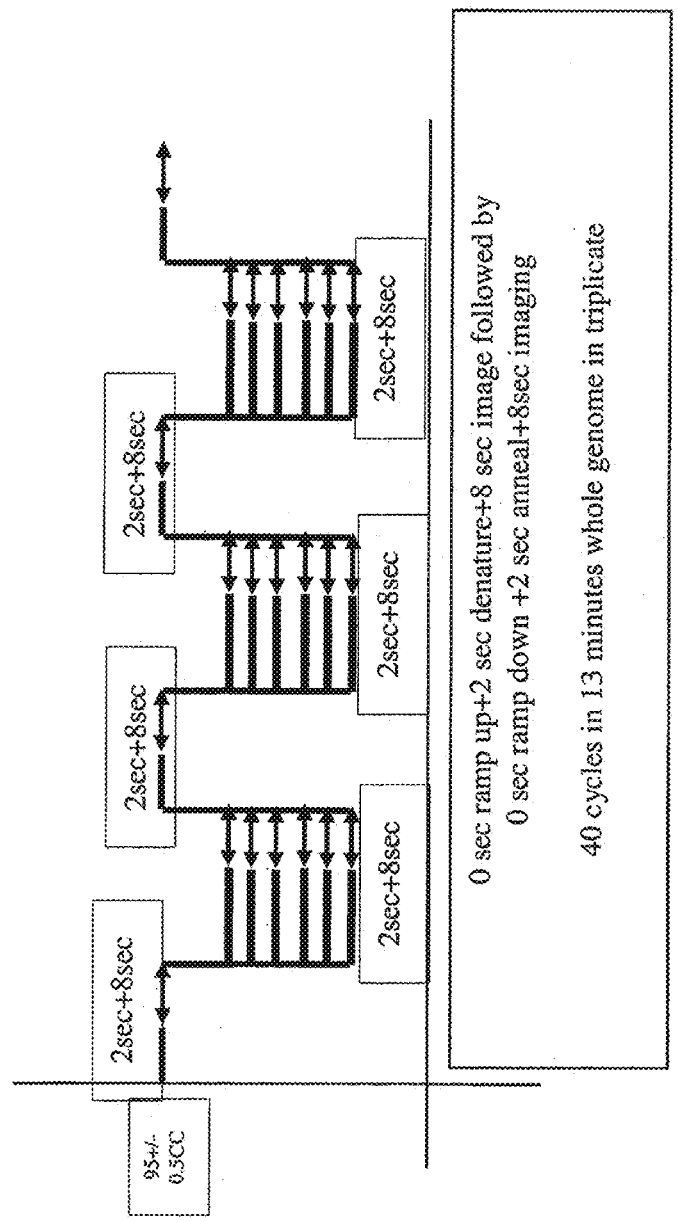
FIG. 14 demonstrates a temperature profile provided by a thermal cycling apparatus of the invention with a heater divided into different temperature zones.

A temperature profile provided by a thermal cycling apparatus of the invention is demonstrated in FIG. 14. In this example, the 6 different temperature zones of the first heater are represented by separate lower temperatures than the 95° C. uniform temperature provided by the second heater. For example, when amplifying an entire human genome with the chips, systems, and apparatuses of the invention, 40 cycles can be performed in less than about 15 minutes, 10 minutes or even 5 minutes in order to amplify every gene (about 30,000) of the genome.

The body of the apparatus for providing cycling at least two temperature levels is configured to receive a sample holder. The sample holder can be held in place within the body by a variety of means, including vacuum force. In an embodiment, the body comprises a vacuum chuck for holding the sample holder firmly in place allowing for a heater to be placed into thermal contact with the sample holder. Clamps, pins, adhesives, slots, or any other method of securing can be incorporated into the body as configured to receive the sample holder as would be obvious to those skilled in the art.

The apparatus can also further comprise sensors to determine the position of the first and second orientations of a heating element in respect to the sample holder.

In another aspect of the invention, an apparatus for conducting a chemical reaction involving cycling at least two temperature levels comprises: a body configured to receive a chip comprising a plurality of nanowells for containing the chemical reaction; and a first heater providing a first temperature and a second heater providing a second temperature, wherein the first heater and the second heater are configured to be movable between a first and a second orientation, and wherein the first orientation places the heater in thermal contact with the sample holder and the second orientation does not place the heater in thermal contact with the sample holder.

In an embodiment, the plurality of nanowells are addressable, wherein the nanowells are arranged according to a predetermined set of temperatures, such that at least one of the nanowells is addressed to indicate the predetermined temperature for running the chemical reaction within said nanowell.

In another embodiment, the first heater comprises a plurality of temperature zones. The plurality of temperature zones can correspond to the predetermined set of temperatures according to which the units are arrayed.

The first and second heaters can move between the first and second orientations according to a protocol. In an embodiment, the apparatus can further comprise a motor for moving the first and second heaters between the first and second orientations.

In an embodiment, the first heater can provide a temperature gradient. Examples of types of heaters for the first and second heaters include, but are not limited to, a resistive heater and a thermoelectric heater.

In a further embodiment, the apparatus comprises a heat sink in thermal contact with the first heater, the second heater, or both.

In order to monitor temperature, the apparatus can also comprise a plurality of temperature sensors. In an embodiment, the plurality of temperature sensors have at least one temperature sensor assigned to measure the temperature of each temperature zone of the apparatus.

Figure 15:
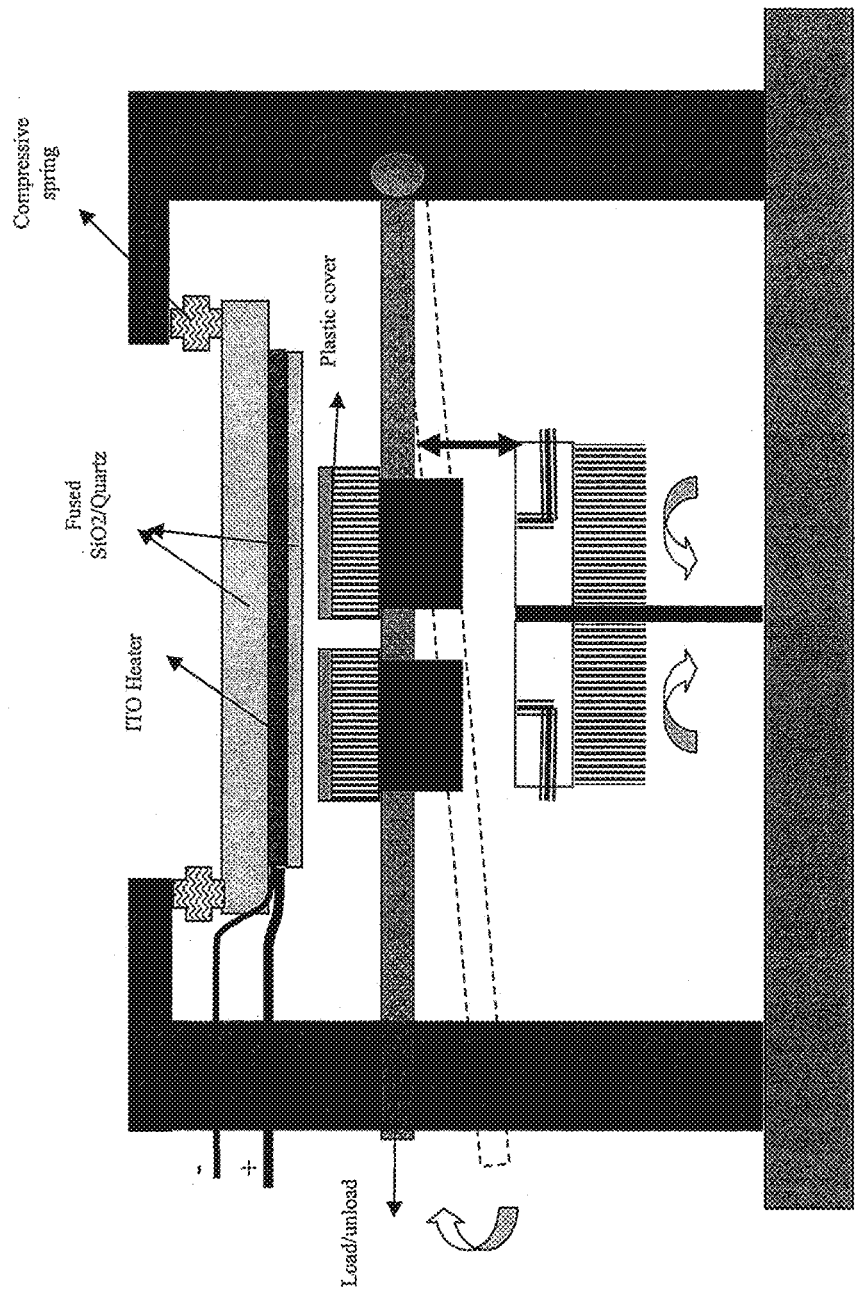
FIG. 15 demonstrates an exemplary apparatus or system of the invention, wherein the apparatus comprises a top cover slide and a heater capable of providing force to bring a chip or chemical reaction into optical and/or thermal contact with the top cover slide.

An exemplary apparatus and system 1500 of the invention is illustrated in FIG. 15. A chip 1510 can be loaded into an apparatus for conducting a chemical reaction involving cycling at least two temperature levels. The chip 1510 can be set in place by any method capable of holding them in place, such as a vacuum or a clip. The chip can also be placed within the apparatus by sliding the chip into place against a stop or a wall, which aligns the chip in a proper position. The chip can be placed on a sample holder 1520 that is capable of moving up and down. The sample holder can be configured to couple to a heater 1530 of the apparatus 1500.

In an embodiment, the chip 1510 and/or wells of the chip are sealed by a thin plastic cover 1512, e.g., a standard PCR tape for covering a chip or a nanowell plate. The PCR tape can be made of a transparent material, such as polyethylene, and can be removable and sometimes can be replaceable. Transparent oil can also be used to cover the wells and/or surface of the chip 1510. In an embodiment, the chip 1510 and/or wells are covered by oil and a cover.

In an embodiment, the cover 1512 covering the chip 1510 is not removed before placing the chip into a thermal cycling apparatus of the invention. After the chip is in place within the apparatus, the heater 1530 can provide a force to the chip 1510 that brings the chip 1510 into optical or thermal contact with a top cover slide 1540. The top cover slide 1540 can be made of a transparent material or any material that allows optics to view a reaction of the chip. Materials that can be used as the top cover slide include, but are not limited to, glass, silica, silicon, and polymers or plastics as would be obvious to those skilled in the art.

The top cover slide 1540 may also comprise a heater 1542, such as an indium tin oxide (ITO) heater, that can heat the top of the chip 1510 or the cover of the chip 1512 and/or wells. A heater 1542 of the top cover slide can be used to balance the temperature at the surface of the chip such that condensation does not occur at the surface or opening of a unit on the chip. For example, when a PCR reaction is run, the liquid components of the reagents and/or sample may heat to a point where they condense on the surface or cover of the reaction unit, or reaction well. Condensation can interfere with an optical system used to monitor the reaction within the unit. In an embodiment of the invention, as demonstrated in FIG. 15, the heater 1530 of the apparatus can provide a force that brings the chip 1510 into thermal contact with a top cover slide 1540 comprising a heater 1542, which can balance the temperature at the surface of the chip 1510 to prevent condensation. Also shown in FIG. 15, the top cover slide 1540 may be connected to a bridge 1550 of the apparatus by a pair of springs or compressive devices 1552. The springs or other devices 1552 can relieve some of the pressure on the top cover slide 1540 from the force of the heater 1530 against the chip 1510, making the apparatus and system more robust. Any method of or device for pressure damping may be used to couple the top cover slide to a bridge of the apparatus.

In the exemplary system and apparatus in FIG. 15, a chip 1510 can be unloaded or loaded through the side of the thermal cycling apparatus 1500. A heater 1530 of the apparatus can then be moved into an orientation in thermal contact with the chip 1510 and also provide a force that brings the chip into thermal contact with a top cover slide 1540. In FIG. 15, the chip has a plastic cover 1512 covering the wells. Also in FIG. 15, the top cover slide 1540 comprises fused $SiO_2$/Quartz material and also comprises an ITO heater 1542. The ITO heater 1542 is operated by electric leads 1544 connected to the ITO heater as shown in FIG. 15. The top cover slide 1540 is then connected to a bridge 1550 of the apparatus by a compressive spring 1552 that provides stress relief within the system. The spring 1552 can also serve to improve the thermal contact of the chip 1510 to both a heater 1530 of the apparatus and a heater of the top cover slide 1540.

In practice, controlling a heating element and hence the temperature of the reaction sample, can be effected by processing a predetermined algorithm stored on a computer readable medium operatively linked to the heating element. The movement of a heating element can also be controlled by a protocol or algorithm, which can be provided by a computer or stored on a computer readable medium. In other aspects, the controlling step may involve processing temperature or movement sensor signals retrieved from a temperature sensor element that is operatively linked to a unit of a sample holder or chip based on protocols stored on a computer readable medium. This can be achieved by employing conventional electronics components for temperature control that may process either analog or digital signals. Preferably, the electronics components are run on a feedback control circuitry. They can control the temperature of one unit, but more often the temperature of multiple units that collectively form one temperature zone or the temperature of the zone itself. In certain embodiments, the temperatures of the different zones are separately controlled. The thermal cycling profile and duration will depend on the particular application in which the subject chip is to be employed.

Systems

The subject chips can be provided with an optical system capable of detecting and/or monitoring the results or the progress of chemical reactions taking place in the chips. Such optical system achieves these functions by first optically exciting the reactants, followed by collecting and analyzing the optical signals from the reactants of the chip. The optical system applicable for the present invention comprises three elements, namely the optical excitation element, the optical transmission element, and the photon-sensing element. The optical system may also comprise, optionally, an optical selection element.

Figure 16:
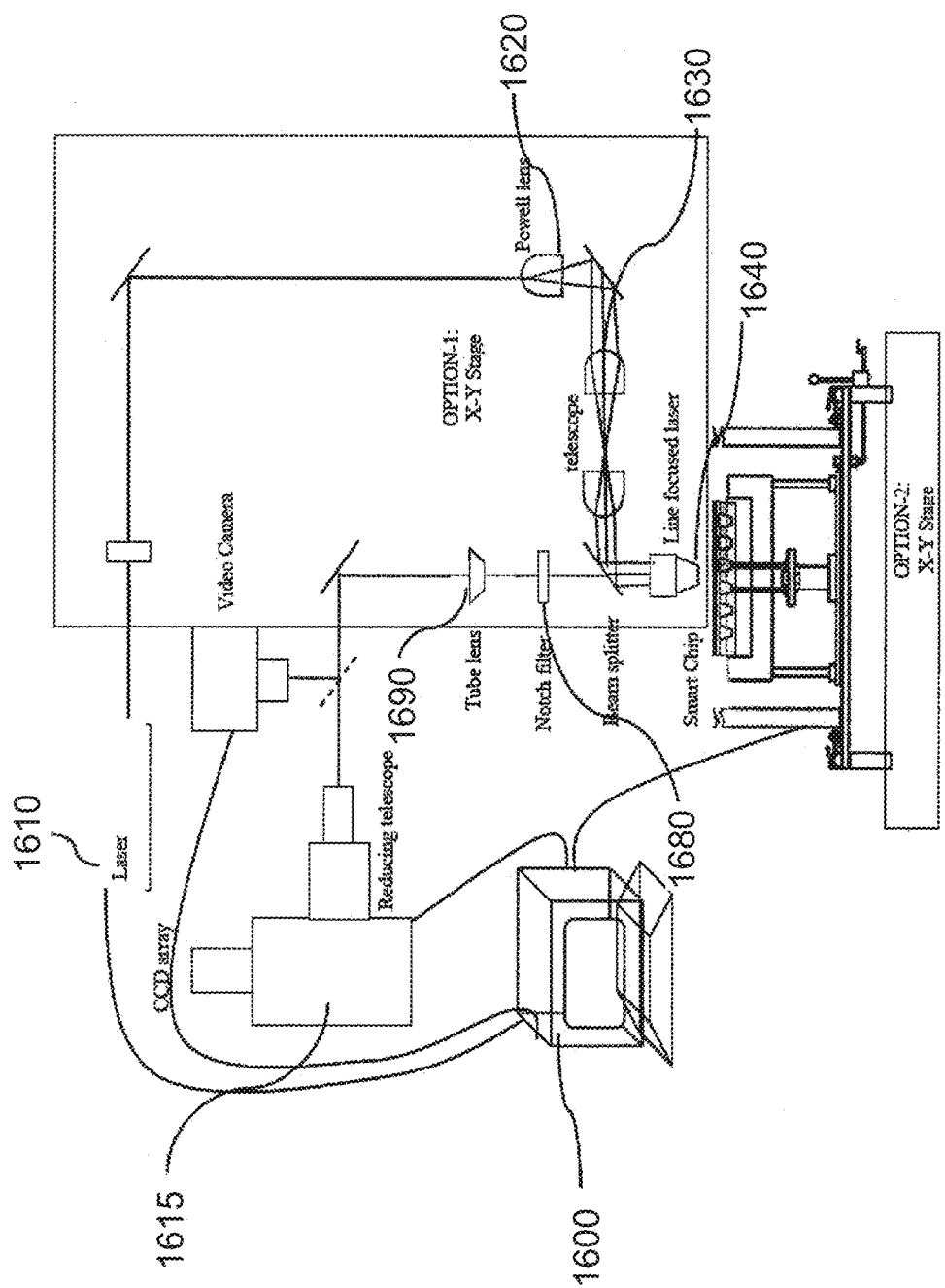
FIG. 16 is a schematic drawing of one embodiment of the thermocycling system of the invention.

FIG. 16 is a representative block diagram showing a representative example of the instrumentation in an experimental setup. FIG. 16 shows a computer system (or digital device) 1600 connected to a laser 1610 as a representative example of an optical excitation element. The optical excitation element acts as the source of excitation beams used to optically excite the reactants contained in the nanowells. This element encompasses a wide range of optical sources that generate light beams of different wavelengths, intensities and/or coherent properties. Representative examples of such optical excitation sources include, but are not limited to, lasers, light-emitting diodes (LED), ultra-violet light bulbs, and/or white light sources.

The optical transmission element used in the present invention serves two functions. First, it collects and/or directs the optical excitation sources to the reactants inside the nanowells of the chips. Second, it transmits and/or directs the optical signals emitted from the reactants inside the nanowells of the chips to the photon-sensing element. The optical transmission element suitable for use in the present invention encompasses a variety of optical devices that channel light from one location point to another. Non-limiting examples of such optical transmission devices include optical fibers, optical multiplexers (MUX) and de-multiplexers (DE-MUX), diffraction gratings, arrayed waveguide gratings (AWG), optical switches, mirrors, lenses, collimators, and any other devices that guide the transmission of light through proper refractive indices and geometries.

The photon-sensing element analyzes the spectra of the optical signals coming from the reactants inside the nanowells. Suitable photon-sensing element can detect the intensity of an optical signal at a given wavelength, and preferably can simultaneously measure the intensities of optical signals across a range of wavelengths. Preferably the element may also provide spectrum data analyses to show the spectrum peak wavelength, spectrum peak width, and background spectrum noise measurements. Representative examples of suitable photon-sensing element for the present invention are avalanche photo diodes (APD), charge-coupled devices (CCD), electron-multiplying charge-coupled device (EMCCD), photo-multiplier tubes (PMT), photo-multiplier arrays, gate sensitive FET's, nano-tube FET's, and P-I-N diode. As used herein, CCD includes conventional CCD, electron-multiplying charge-coupled device (EMCCD) and other forms of intensified CCD.

While the subject optical systems can be assembled using many combinations of the various elements, a useful assembly for analyzing the spectra of the excited reactants comprises an optical transmission element and a photon-sensing element. Such assembly is also referred to herein as "spectrum analyzer".

Where desired, the optical system of the present invention can include an optical selection element. This element selects and/or refines the optical properties of the excitation beams before they reach the reactants contained in the nanowells. The optical selection element can also be employed to select and/or refine the optical signals coming from the reactants in the nanowells before the signals reach the photon-sensing element. Suitable optical selection element can select and modify a wide range of optical properties, including but not limited to, polarization, optical intensities, wavelengths, phase differences among multiple optical beams, time delay among multiple optical beams. Representative examples of such optical selection elements are polarization filters, optical attenuators, wavelength filters (low-pass, band-pass or high-pass), wave-plates and delay lines.

The aforementioned optical elements can adopt a variety of configurations. They can form integral parts of the subject chips or remain as separate units. All of these elements are commercially available. Accordingly, in one embodiment, the present invention provides a chip in which the optical transmission and photon-sensing elements are fabricated into the chip substrate. In one aspect, the photon-sensing element is integrated into each nanowell on the chip that is to be monitored. In another aspect, more than one type of photon-sensing element is integrated into the nanowell to enhance the detection capability or efficiency. In another aspect, the photon-sensing element can be fabricated along the side or at the base of the nanowell, or as part of the cover of the nanowell. Photon-sensing elements suitable for such configuration include but are not limited to avalanche photo diode, charge coupled devices (including conventional CCD, electron-multiplying charge-coupled device (EM-CCD) and other forms of intensified CCD), gate sensitive FET's, nano-tube FET's, P-I-N diode. Avalanche photo diode is particularly preferred because it permits detections of a single photon by amplifying the signal through an avalanche process of electron transfer. These elements together with the supporting circuitry can be fabricated as part of the subject chips using standard IC processing techniques described herein or known in the art.

In another embodiment, the present invention provides an apparatus in which the chip and the optical systems remain as separate units. One aspect of this embodiment encompasses an apparatus for conducting a chemical or biological reaction requiring cycling at least two temperature levels over a multiple-cycle period. The apparatus comprises a chip of the present invention, and an optical system that is operatively coupled to the chip and that detects an optical signal coming from the nanowell. Preferably, the optical signals detected are related to the amount of product of the chemical reaction taking place in the nanowell.

FIG. 16 illustrates an exemplary optical system of this aspect. In an exemplary embodiment, this system includes an optical transmission element, such as a tunable laser 1610, or Xenon lamp, controlled by the computer or other digital setup 1600. The laser is then focused further to provide uniform distribution across all the nanowells using a Powell lens 1620, a telescope 1630, and/or a line focused laser 1640. The optical signals coming from the nanowells on the chip are collimated by a lens 1690, such as a tube lens, and are passed through a tunable filter 1690, either a low-pass, high-pass, or notch-filter, to a charge-coupled device (CCD) 1615 for spectrum analysis. This particular embodiment offers a low cost solution for monitoring the progress and/or results of chemical reactions taking place in nanowells fabricated on a chip.

In a further embodiment the optical transmission element is moveable being placed on a X-Y stage, as seen in Option 1 of FIG. 16. In an alternative embodiment, the chip is placed on an X-Y stage as seen in Option 2 of FIG. 16.

In a further embodiment feedback control or self learning is provided to achieve optimized chemical reactions at specific nanowells of the substrate. For example, using a fixed position substrate including an array of nanowells in conjunction with a moveable optical transmission element and photon-sensing element, after heating (or providing a series of heating and/or cooling steps) with one or more optical transmission units, the photon-sensing element can detect the outcome of a desired chemical reaction in a specific nanowell. Upon analysis of each chemical reaction in a given nanowell based on the detection step, suitable corrections (for example, raising or lowering reaction temperatures or durations of reaction cycles) can be implemented in subsequent cycle rounds of heating and/or cooling to optimize the chemical reaction as needed. This process can be repeated using repeated passes of the transmission element and sensing element over the various nanowell locations until the desired outcome of a chemical reaction is detected in each nanowell. In this way a given nanowell chemical reaction can be sequentially monitored and manipulated to provide an optimized chemical reaction for the given nanowell. Different conditions may be required at different nanowell locations based on the unique properties of the individual reactions (for example, where different primers and templates are used in a PCR reaction). Thus, the apparatus of the present invention can be used in conjunction with a feed back loop process directed to each nanowell location, to optimize the chemical reaction at every location on a substrate.

In an exemplary embodiment, a Chungara series CCD camera can be used. The Chungara CCD camera can be used for the most demanding applications in low noise and long exposure imaging in areas such as astronomy and spectroscopy. The Chungara CCD controller is able to read a wide range of CCDs, because it is based on modularity and common hardware architecture. For instance, example CCDs that can be used range from the 1536×1024 Kodak KAF-1602 CCD to the 4096×4096 Kodak KAF-16801 CCD. The camera can be linked to a host computer thru an ethernet link or wireless connection allowing a large distance between the computer and the CCD camera.

In another embodiment, the present invention provides a system in which the chip, apparatus and the optical systems are separate units. In one embodiment, the apparatus, system, chip of the present invention, a thermal cycling apparatus or heating element of the invention, and an optical system that is operatively coupled to the chip and that detects an optical signal coming from an addressable unit of the chip. Preferably, the optical signals detected are related to the amount of product of the chemical reaction taking place in the unit.

In another preferable embodiment, the amplified nucleic acids in the subject chips are detected by the subject optical systems operatively coupled to the chips. The optical systems are capable of transmitting appropriate excitation beams to the reactants in the amplification reactions, collecting and analyzing the emitted optical signals from the reactants. Preferably, the optical signals detected are indicative of the amount of amplified nucleic acid in the amplification reaction over a multiple-cycle period. In certain aspects, the optical system transmits excitation beams into the wells containing the reaction samples at a plurality of times during the amplification, and monitors the optical signals coming from the nanowells at each of the plurality of times. By analyzing the relative intensities of the optical signals, preferably over a multiple-cycle period, one can monitor quantitatively the progression of the amplification reaction. Typically, the optical signals being monitored are luminescent signals. Detecting and/or monitoring the amplification products can be performed without opening the nanowell once the amplification is initiated.

Figure 17:
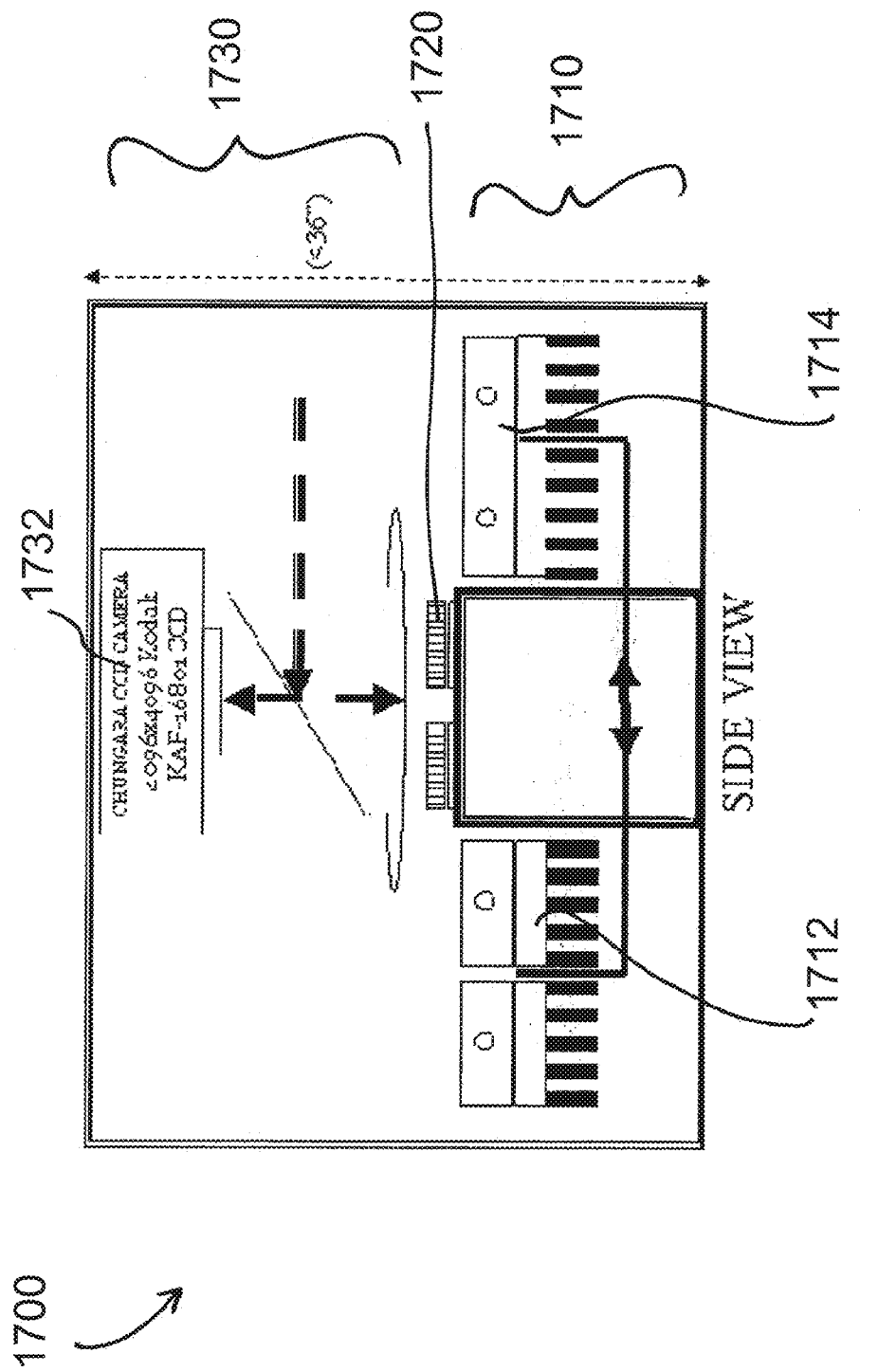
FIG. 17 illustrates an exemplary system of the invention comprising a chip, a heating apparatus, and an optical system for analyzing the reaction results.

FIG. 17 demonstrates an example system 1700 of the invention with a thermal cycling apparatus 1710 with a first 1712 and second heater 1712 that can be moved between a first and second orientation, and a chip 1720 with an addressable array of units based on predetermined temperatures. In this example, the optical system 1730 operatively coupled to the chip 1720 and apparatus 1710 is a Chungara CCD camera 1732. As shown by the side view in FIG. 17, the heaters 1712, 1714 can move independently and brought into thermal contact with a chip 1720 of the invention to provide rapid thermal cycling of a large number of chemical reactions, such as PCR amplification reaction of an entire genome.

Figure 18:
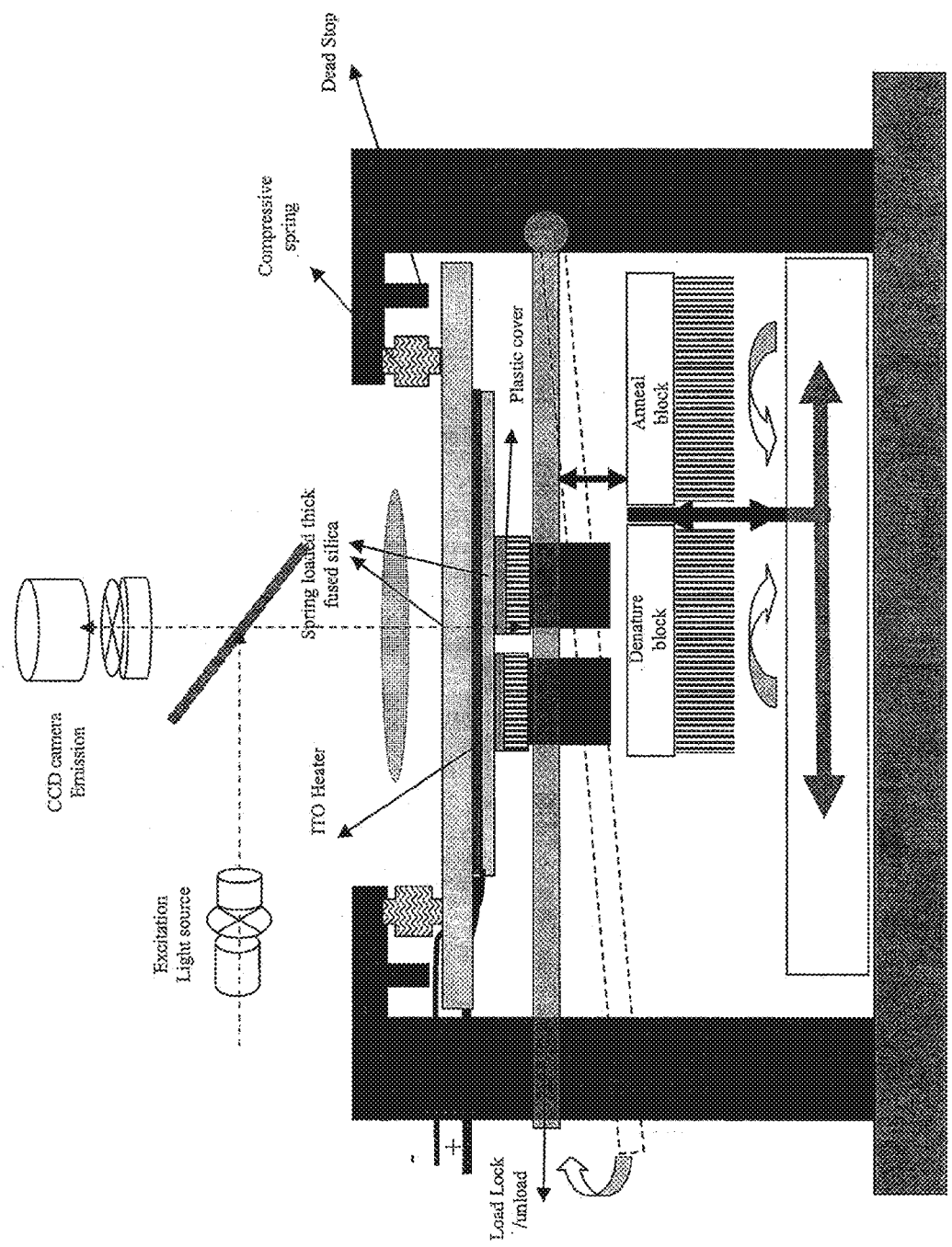
FIG. 18 demonstrates an example system of the invention comprising an optical system, a heating apparatus, and a chip for conducting a chemical reaction.

FIG. 18 demonstrates an example system 1800 of the invention comprising an optical system 1810, a heating apparatus 1820, and a chip 1830 for conducting a chemical reaction. The heating apparatus 1820 of the system may be a thermal cycling device for conducting a PCR reaction. As shown in FIG. 18, the heating apparatus can comprise a denature block 1822 and an anneal block 1824 for conducting PCR. The heating apparatus 1820 is also movable both horizontally and vertically as indicated by the arrows in FIG. 18. A chip 1830 is inserted on a sample holder 1840 that can move vertically. The chip 1830 and/or nanowells of the chip may or may not be covered by a plastic cover 1832. The heater 1820 can force the sample holder 1840 into thermal contact with a top cover slide 1850 comprising a thin film ITO heater 1852. The top cover slide 1850 is connected to the system 1800 by a compressive spring 1854 to permit better thermal contact between the sample holder 1840 and heaters 1820, 1852 of the system. The system 1800 may also comprise a dead stop 1856 to prevent the top cover slide 1850 from compressing into the optical system 1810.

In FIG. 18, the optical system 1810 comprises a CCD camera 1812, an excitation light source 1814, optics 1816, and an optical filter 1818. The system may comprise a plurality of optical systems. In another embodiment, the system comprises a plurality of CCD camera, excitation light sources, optics, or optical filters. The optical system 1810 can function to receive information from a chemical reaction that occurs in the chip 1830 when the chip 1830 is in thermal contact with the heating apparatus 1820.

Figure 19:
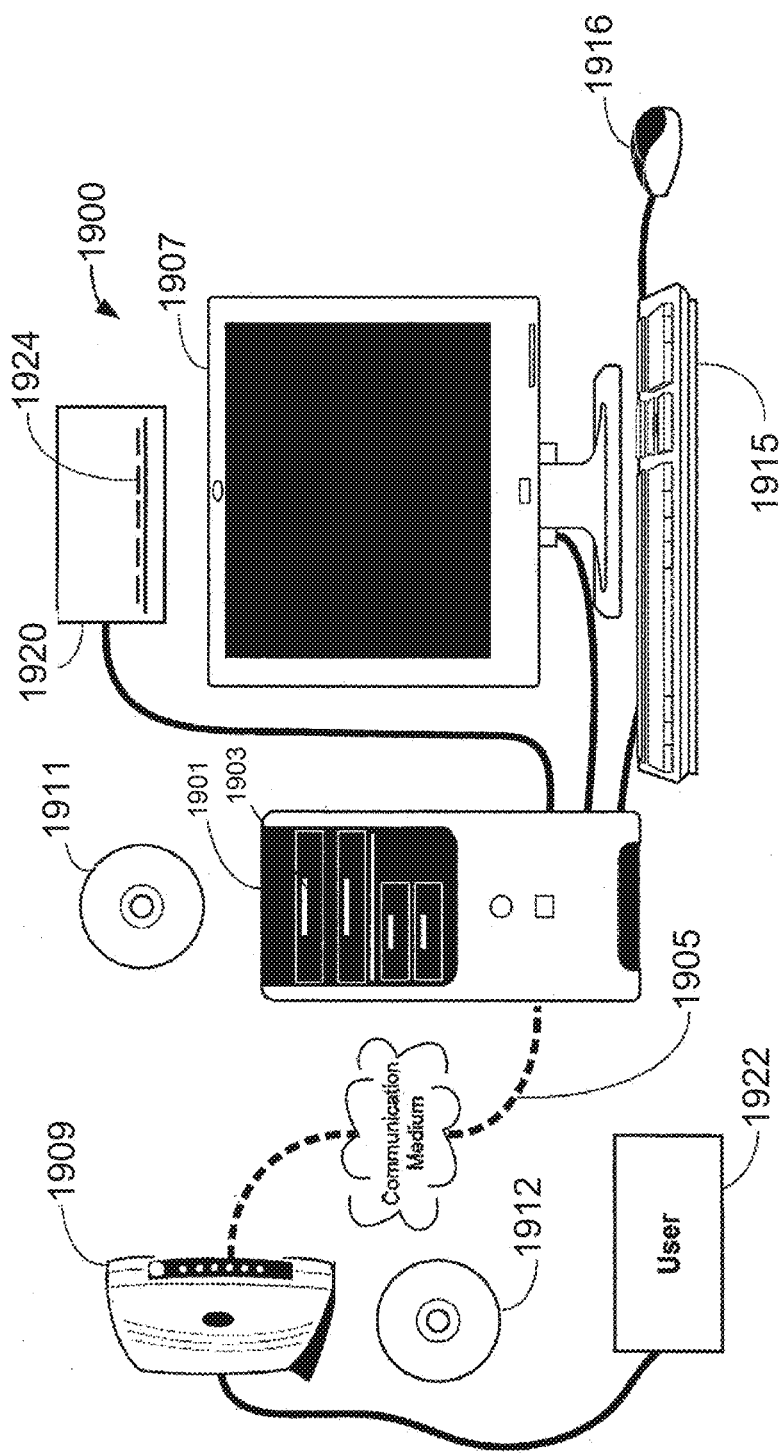
FIG. 19 is a block diagram showing a representative example logic device in communication with the system according to the specific embodiments of the invention.

FIG. 19 is a block diagram showing a representative example logic device through which reviewing or analyzing data relating to the present invention can be achieved. Such data can be in relation to a genotype, a genetic make up or a disease, disorder or condition in an individual. FIG. 19 shows a computer system (or digital device) 1900 connected to an apparatus 1920 for use with an apparatus 1924 to, for example, produce a result. The computer system 1900 may be understood as a logical apparatus that can read instructions from media 1911 and/or network port 1905, which can optionally be connected to server 1909 having fixed media 1912. The system shown in FIG. 19 includes CPU 1901, disk drives 1903, optional input devices such as keyboard 1915 and/or mouse 1916 and optional monitor 1907. Data communication can be achieved through the indicated communication medium to a server 1909 at a local or a remote location. The communication medium can include any means of transmitting and/or receiving data. For example, the communication medium can be a network connection, a wireless connection or an internet connection. Such a connection provide for communication over the World Wide Web. It is envisioned that data relating to the present invention can be transmitted over such networks or connections for reception and/or review by a party 1922. The receiving party or user 1922 can be a patient, a health care provider or a health care manager. In one embodiment, a computer-readable medium includes a medium suitable for transmission of a result of an analysis of a biological sample. The medium can include a result regarding a genotype, a genetic make up or a disease condition or state of a subject, wherein such a result is derived using the methods described herein.

Uses of the Present Invention

The subject chips and apparatuses for thermal cycling have a wide variety of uses in chemical and biological applications where controllable temperatures are desired. The methods, chips, and apparatuses of this invention are preferably performed with equipment which aids in coupling one or more steps of the process, including handling of the chips, thermal cycling, and imaging. Accordingly, the present invention provides systems for simultaneously determining the genetic expression profile in a biological sample obtained from an individual member of a species relative to a standard genome for said species.

In one embodiment, the invention can be used to vary and/or maintain temperature of a reaction sample. Varying and/or maintaining temperature of a reaction sample are required in a wide range of circumstances including but not limited to discerning protein-protein interaction, examining DNA or RNA hybridization, and performing enzymatic reaction. The method involves placing the reaction sample into a nanowell fabricated in a chip that is in thermal contact with a heating element, and applying a voltage to the heating element.

In another embodiment, the subject chips apparatuses for thermal cycling are used for conducting a chemical reaction that involves a plurality of reaction samples and requires cycling at least two temperature levels. The process involves (a) providing a chip comprising an array of units as described herein; (b) placing the plurality of reaction samples into the units of the chip; and (c) controlling the heating element to effect cycling at least two temperature levels.

Practicing the subject method generally proceeds with placing the reaction sample into a nanowell of the subject chip that is in thermal contact with a heating element. Where desired, the reaction sample can be applied by a dispensing system operatively coupled to the subject chip. A variety of dispensing instruments, ranging from manually operated pipettes to automated robot systems are available in the art. Preferred dispensing instruments include a piezo-electric nano-dispenser.

The subject chips and apparatuses are particularly suited for conducting quantitative nucleic acid amplification. Accordingly, the present invention provides a method for monitoring the formation of a nucleic acid amplification reaction product, preferably in real time. In certain preferred embodiments, the amplified nucleic acids contained are directly monitored by the photon-sensing elements integrated into the chips. The photon-sensing element registers the intensities of the optical signals that are reflective of the amount of the amplified nucleic acids at any time being examined during the amplification reaction. The optical signals may be any kind of luminescent signals emitted upon exciting the labeled reactants with appropriate incident beams.

The subject methods of amplifying and detecting a target nucleic acid have broad spectrum of utility in, for example drug screening, disease diagnosis, phylogenetic classification, genotyping individuals, parental and forensic identification.

In an embodiment, a system, chip, apparatus, or method of the invention can be used to discover therapeutically-relevant biomarkers. For example, the invention could be used to identify biomarkers for chronic obstructive pulmonary disease (COPD) and lung cancer.

At a more fundamental level, amplification and detection of the target nucleic acids may be used in identification and quantification of differential gene expression between diseased and normal tissues, among different types of tissues and cells, amongst cells at different developmental stages or at different cell-cycle points, and amongst cells that are subjected to various environmental stimuli or lead drugs.

In various configurations of the present invention, a method is disclose for supplying to a consumer assays useful in obtaining structural genomic information, such as the presence or absence of one or more single nucleotide polymorphisms (SNPs), and functional genomic information, such as the expression or amount of expression of one or more genes. As such, the assays can be configured to detect the presence or expression of genetic material in a biological sample. The method includes providing a user interface configured for receiving orders for stock assays, providing a user interface configured for receiving requests for design of custom assays and for ordering said assays, and delivering to the consumer at least one custom or stock assay in response to an order for the one custom or stock assay placed by the consumer. In certain other aspects, the present invention includes a system, apparatus, chip, and methods for constructing a system for providing to a consumer assays configured to detect presence or expression of genetic material. In an embodiment, the chips can be customized according to a user's needs.

The present invention provides devices and methods for containing and handling small quantities of liquids, including methods and devices for performing amplification reactions on liquid samples containing polynucleotides. Embodiments of the present invention include chips for conducting a chemical reaction, including a thermocycled amplification reaction of polynucleotide, in a liquid sample.

The subject chips and other devices find utility in many other chemical and biological applications where controllable temperatures are desired. Such applications include a vast diversity of reactions such as redok reactions, hydrolysis, phosphorylation, and polymerization. Additional applications are directed to discerning interactions involving biological molecules such as proteins, glycoproteins, nucleic acids, and lipids, as well as inorganic chemicals, or any combinations thereof. The chemical reaction may also involve interactions between nucleic acid molecules, between nucleic acid and protein, between protein and small molecules The chemical reaction may take place outside a cell or inside a cell that is introduced into a nanowell of the subject chip.

Of particular significance is the application in detecting the presence of a specific protein-protein interaction. Such application generally employs a proteinaceous probe and a target protein placed in a unit in the subject chip.

In one aspect of this embodiment, the protein-protein interaction is between a target protein (for example an antigen) and an antibody specific for that target. In another aspect, the protein-protein interaction is between a cell surface receptor and its corresponding ligand. In yet another aspect, the protein-protein interaction involves a cell surface receptor and an immunoliposome or an immunotoxin; in other aspects, the protein-protein interaction may involve a cytosolic protein, a nuclear protein, a chaperon protein, or proteins anchored on other intracellular membranous structures.

The terms "membrane", "cytosolic", "nuclear" and "secreted" as applied to cellular proteins specify the extracellular and/or subcellular location in which the cellular protein is mostly, predominantly, or preferentially localized.

"Cell surface receptors" represent a subset of membrane proteins, capable of binding to their respective ligands. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions.

The reaction is typically performed by contacting the proteinaceous probe with a target protein under conditions that will allow a complex to form between the probe and the target. The conditions such as the reaction temperature, the duration of the reaction, the buffer conditions and etc., will depend on the particular interaction that is being investigated. In general, it is preferable to perform the reactions under physiologically relevant temperature and buffer conditions. Physiologically relevant temperatures range from approximately room temperature to approximately 37° C. This can be achieved by adjusting the heating element of the subject chips. Typically, a physiological buffer contains a physiological concentration of salt and at adjusted to a neutral pH ranging from about 6.5 to about 7.8, and preferably from about 7.0 to about 7.5. A variety of physiological buffers is listed in Sambrook et al (1989) supra and hence is not detailed herein.

The formation of the complex can be detected directly or indirectly according standard procedures in the art or by methods describe herein. In the direct detection method, the probes are supplied with a detectable label and when a complex is formed, the probes emitted an optical signal distinct from that of the unreacted probes. A desirable label generally does not interfere with target binding or the stability of the resulting target-probe complex. As described above, a wide variety of labels suitable for such application are known in the art, most of which are luminescent probes. The amount of probe-target complexes formed during the binding reaction can be quantified by standard quantitative assays, or the quantitative methods using the optical systems described above.

The examples and other embodiments described herein are exemplary and are not intended to be limiting in describing the full scope of apparatus, systems, compositions, materials, and methods of this invention. Equivalent changes, modifications, variations in specific embodiments, apparatus, systems, compositions, materials and methods may be made within the scope of the present invention with substantially similar results. Such changes, modifications or variations are not to be regarded as a departure from the spirit and scope of the invention.

What is claimed is:

1. An apparatus comprising at least first and second heating elements in thermal contact with a chip comprising a substrate and an array of nanowells, wherein at least one of the first and second heating elements is configured to move relative to the chip, wherein the first heating element is in thermal contact with the chip from above the chip and the second heating element is in thermal contact with the chip from below the chip, and wherein the second heating element in thermal contact from below the chip is set at a temperature lower than the temperature of the first heating element in thermal contact from above the chip.

2. The apparatus of claim 1, wherein the chip comprises an upper surface and a bottom surface and wherein a first series of nanowells is arranged along one orientation on the upper surface and a second series of nanowells is oriented perpendicular to the first series of nanowells.

3. The apparatus of claim 1, wherein the chip is stationary.

4. The apparatus of claim 1, wherein at least one of the first and second heating elements is capable of heating and cooling.

5. The apparatus of claim 1, comprising a plurality of heating elements corresponding to a plurality of temperature zones.

6. The apparatus of claim 5, wherein the plurality of temperature zones provides a range from about 52° C. to about 95° C.

7. The apparatus of claim 6, wherein the plurality of temperature zones provides a temperature gradient.

8. The apparatus of claim 5, wherein at least one of the temperature zones is set at a temperature ranging from about 52° C. to about 65° C. and at least one other temperature zone is set at a temperature ranging from about 90° C. to about 95° C.

9. The apparatus of claim 8, further comprising at least one other temperature zone set at temperature ranging from about 68° C. to about 72° C.

10. The apparatus of claim 1, wherein at least one of the first and second heating elements is configured to provide an output comprising a spike waveform of temperature over time.

11. The apparatus of claim 1, wherein an individual nanowell in said array has a dimension of about 250 μm in length, about 250 μm in width, and a depth of about 525 μm, or less.

12. The apparatus of claim 1, wherein the chip is operatively coupled to an optical system that detects optical signals.

13. The apparatus of claim 12, wherein the optical system comprises a plurality of optical detectors.

14. The apparatus of claim 1, wherein the nanowells are configured to contain about 100 nl.

15. The apparatus of claim 1, wherein the nanowells are physically isolated nanowells.

* * * * *